(12) United States Patent
Kuhn

(10) Patent No.: US 8,376,987 B2
(45) Date of Patent: Feb. 19, 2013

(54) TWO-CHAMBER INJECTION DEVICE HAVING GAS-PERMEABLE MEMBRANE

(75) Inventor: Bernd Kuhn, Frankfurt am Main (DE)

(73) Assignee: Sanofi-Aventis Deustchland GmbH (DE)

( * ) Notice: Subject to any disclaimer, the term of this patent is extended or adjusted under 35 U.S.C. 154(b) by 0 days.

(21) Appl. No.: 12/815,723

(22) Filed: Jun. 15, 2010

(65) Prior Publication Data

US 2011/0060274 A1    Mar. 10, 2011

Related U.S. Application Data

(63) Continuation of application No. PCT/EP2008/010318, filed on Dec. 5, 2008.

(30) Foreign Application Priority Data

Dec. 19, 2007    (EP) .................................. 07024613

(51) Int. Cl.
    *A61M 37/00*    (2006.01)
(52) U.S. Cl. ........................................................ 604/82
(58) Field of Classification Search ................. 604/82
    See application file for complete search history.

(56) References Cited

U.S. PATENT DOCUMENTS

| 4,226,236 | A  | * | 10/1980 | Genese ........................... 604/89 |
| 4,373,535 | A  |   | 2/1983  | Martell |
| 5,114,421 | A  | * | 5/1992  | Polak ............................ 604/403 |
| 5,971,953 | A  |   | 10/1999 | Bachynsky |
| 6,053,368 | A  | * | 4/2000  | Geimer .................... 222/189.09 |
| 2003/0106824 | A1 | * | 6/2003  | Wilmot et al. ................ 206/439 |
| 2010/0087799 | A1 | * | 4/2010  | Galbraith et al. ............. 604/518 |

FOREIGN PATENT DOCUMENTS

| DE | 102004055870 | 5/2006 |
| EP |      1237596 | 9/2002 |
| WO |    2006/007592 | 1/2006 |

* cited by examiner

*Primary Examiner* — Nicholas Lucchesi
*Assistant Examiner* — Jason Flick
(74) *Attorney, Agent, or Firm* — McDonnell Boehnen Hulbert & Berghoff LLP

(57) ABSTRACT

The invention relates to a two-chamber syringe device comprising a cylinder element (2), a closure element (6), two plungers (3) and (4) and optionally an intermediate plunger (3a), wherein one or more fluid-tight, gas-permeable membranes (8) and optionally valve membranes (15) are arranged in the wall of the cylinder element (2) or in the closure element (6), allowing gas in the chambers to escape from the cylinder element (2) when the plungers (3), (3a) and (4) are displaced in the distal direction.

29 Claims, 15 Drawing Sheets

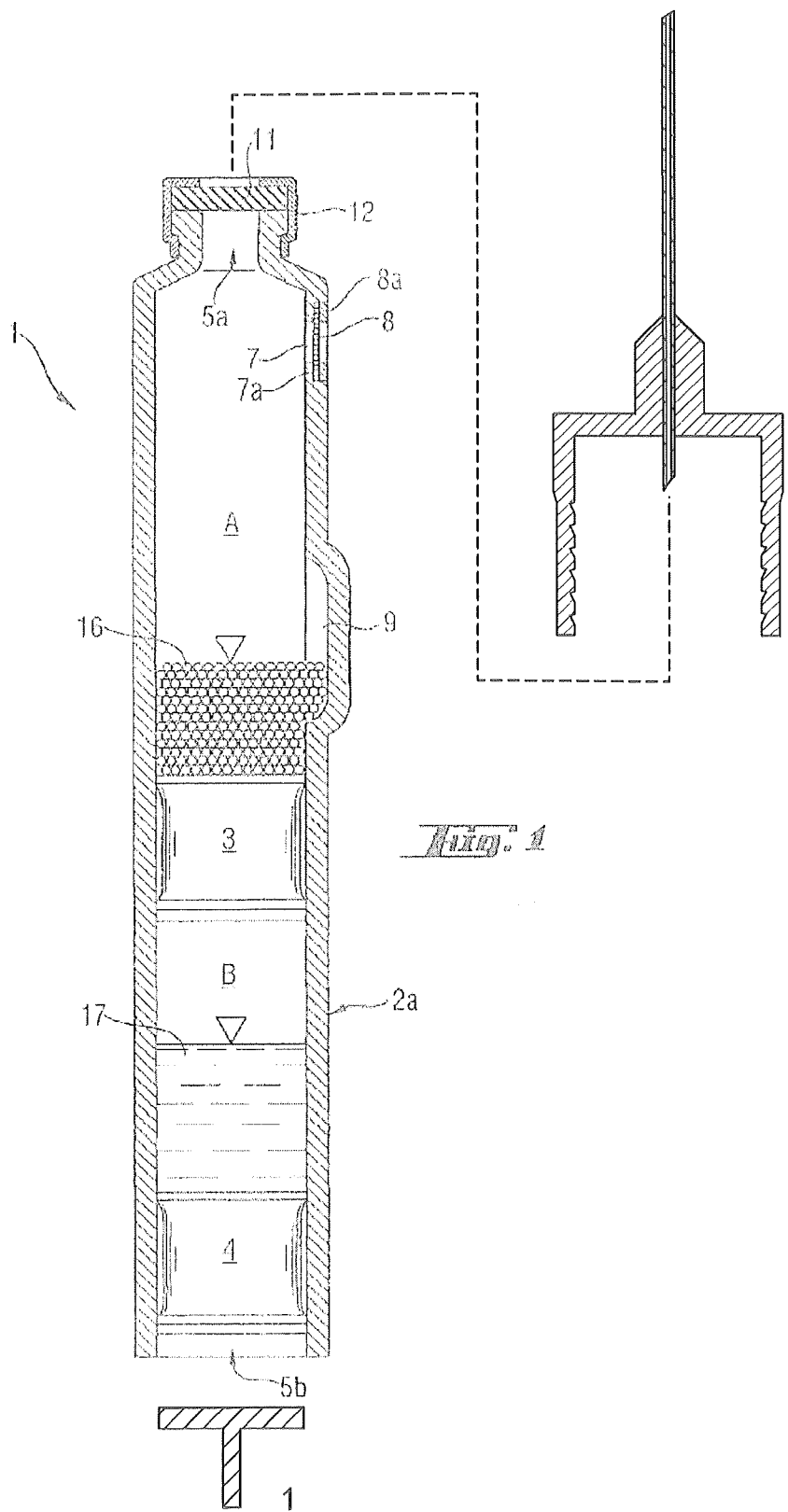

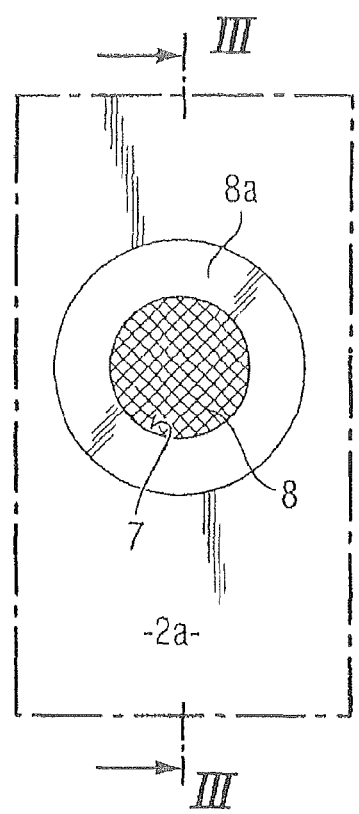
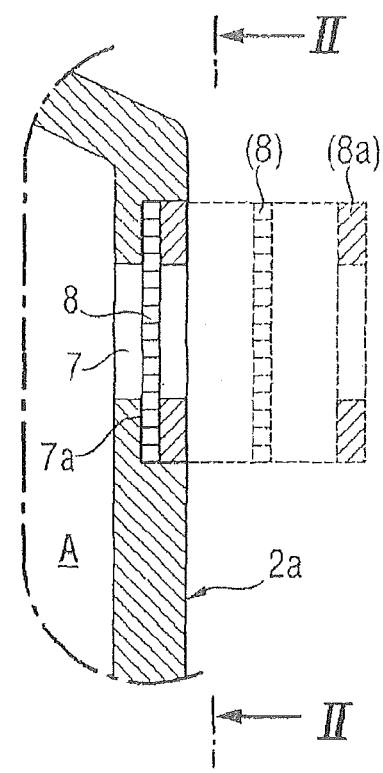

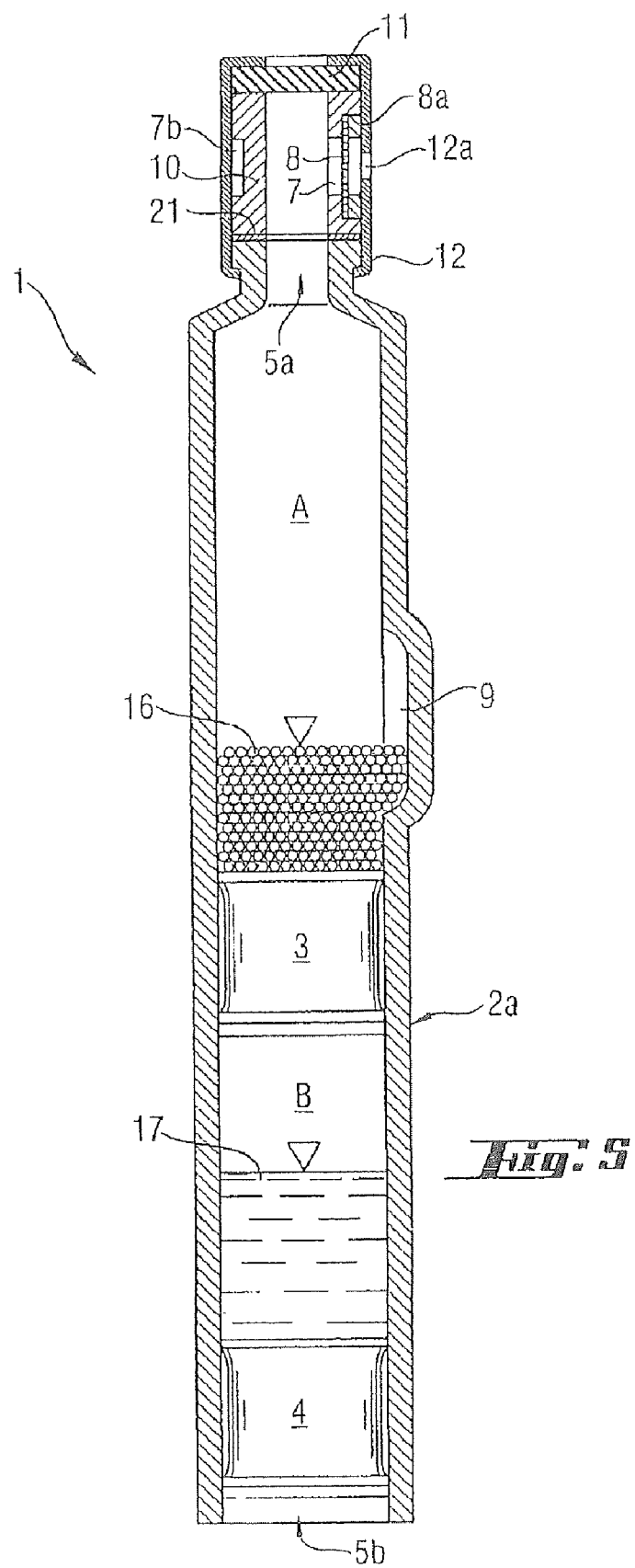

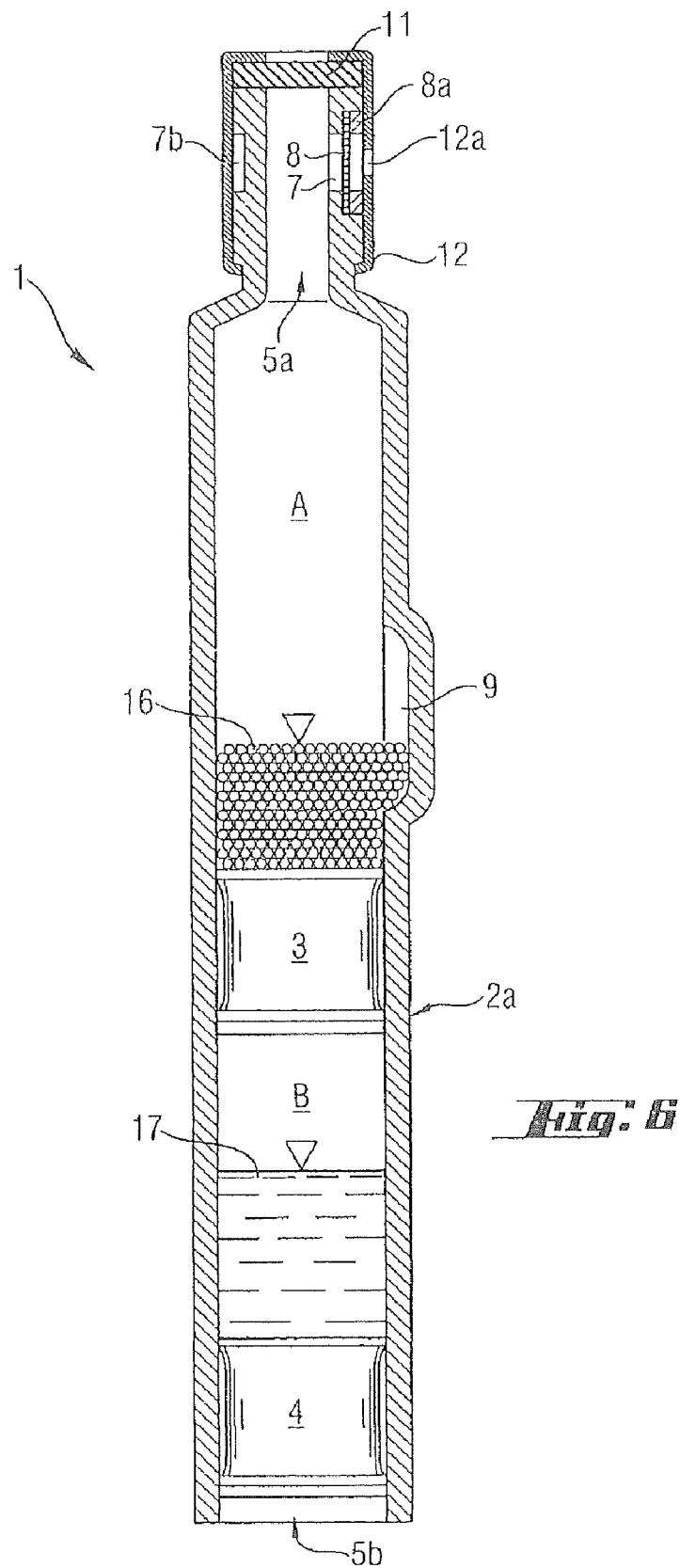

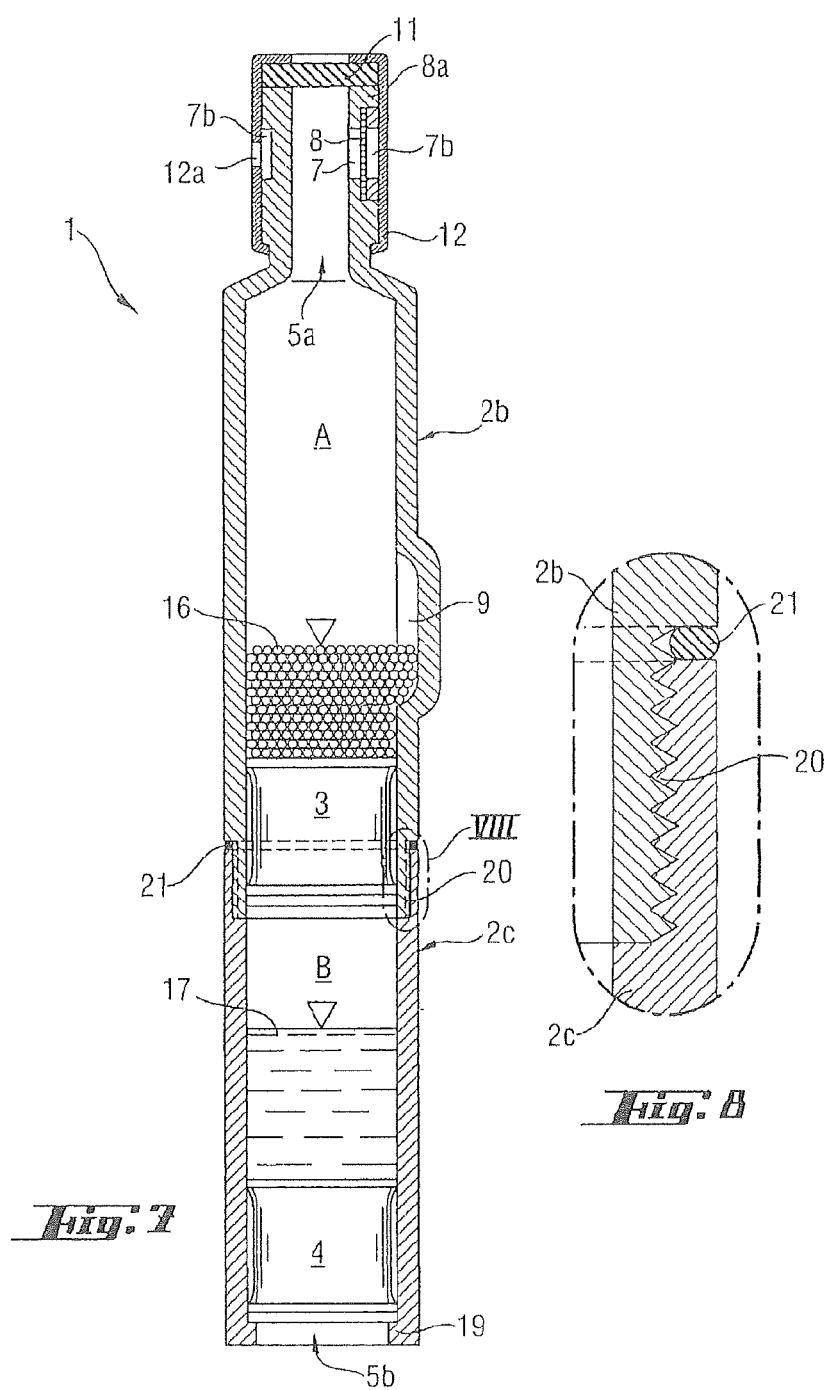

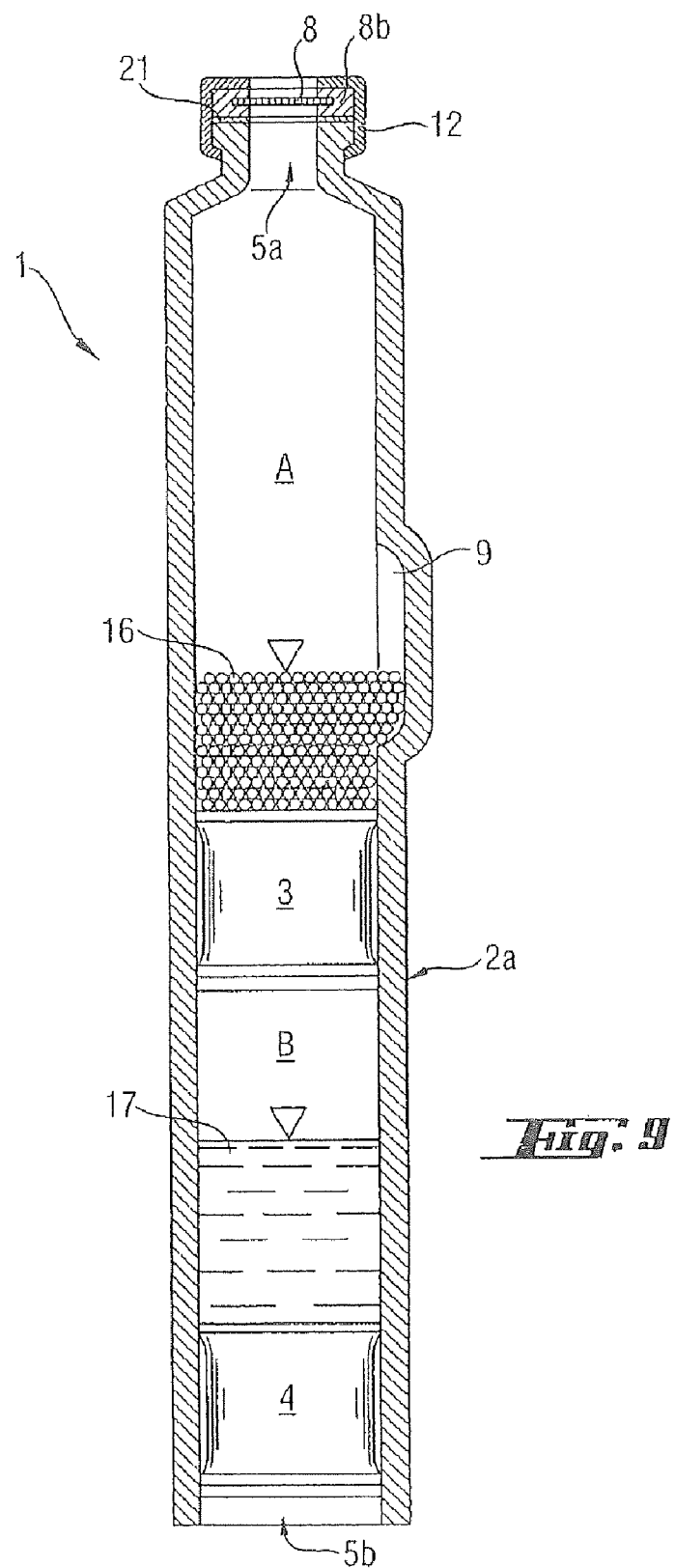

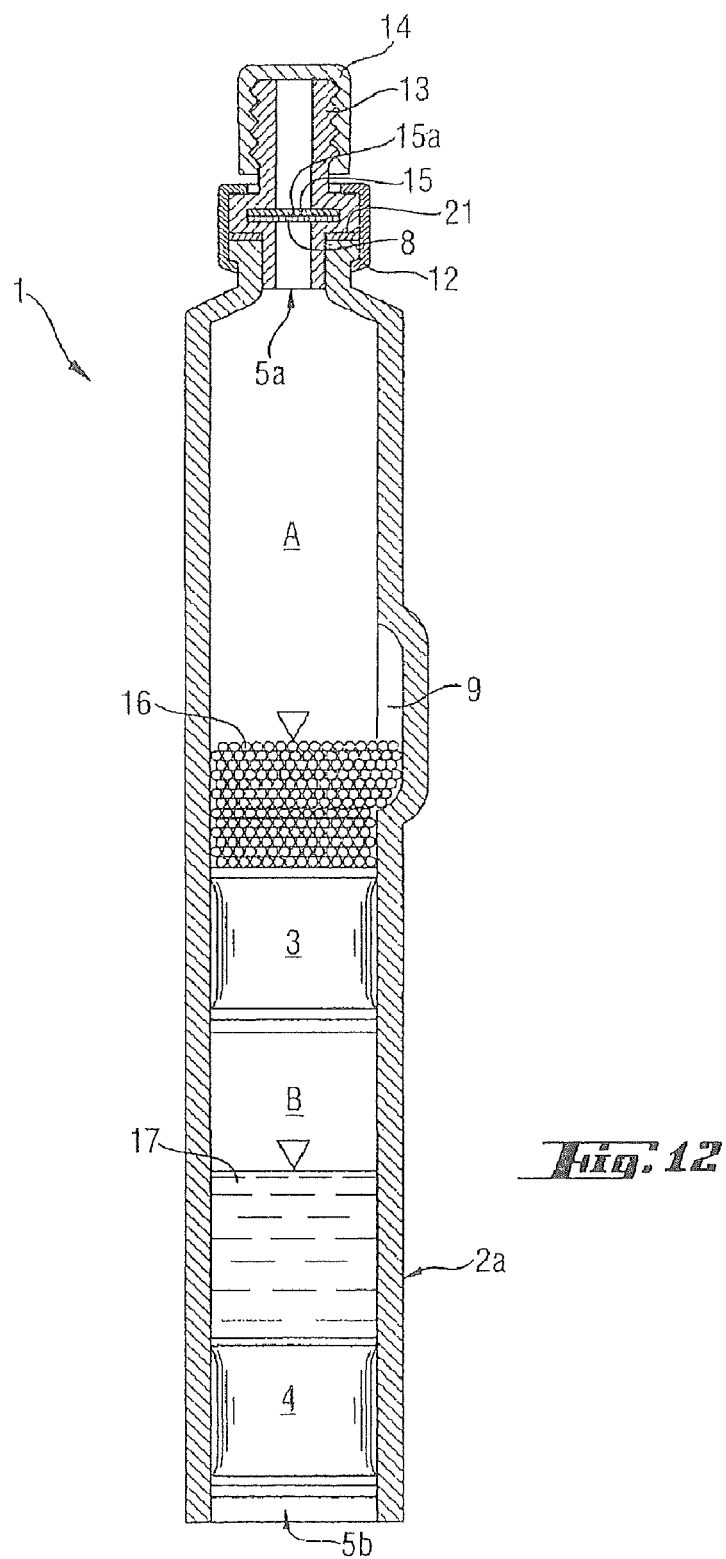

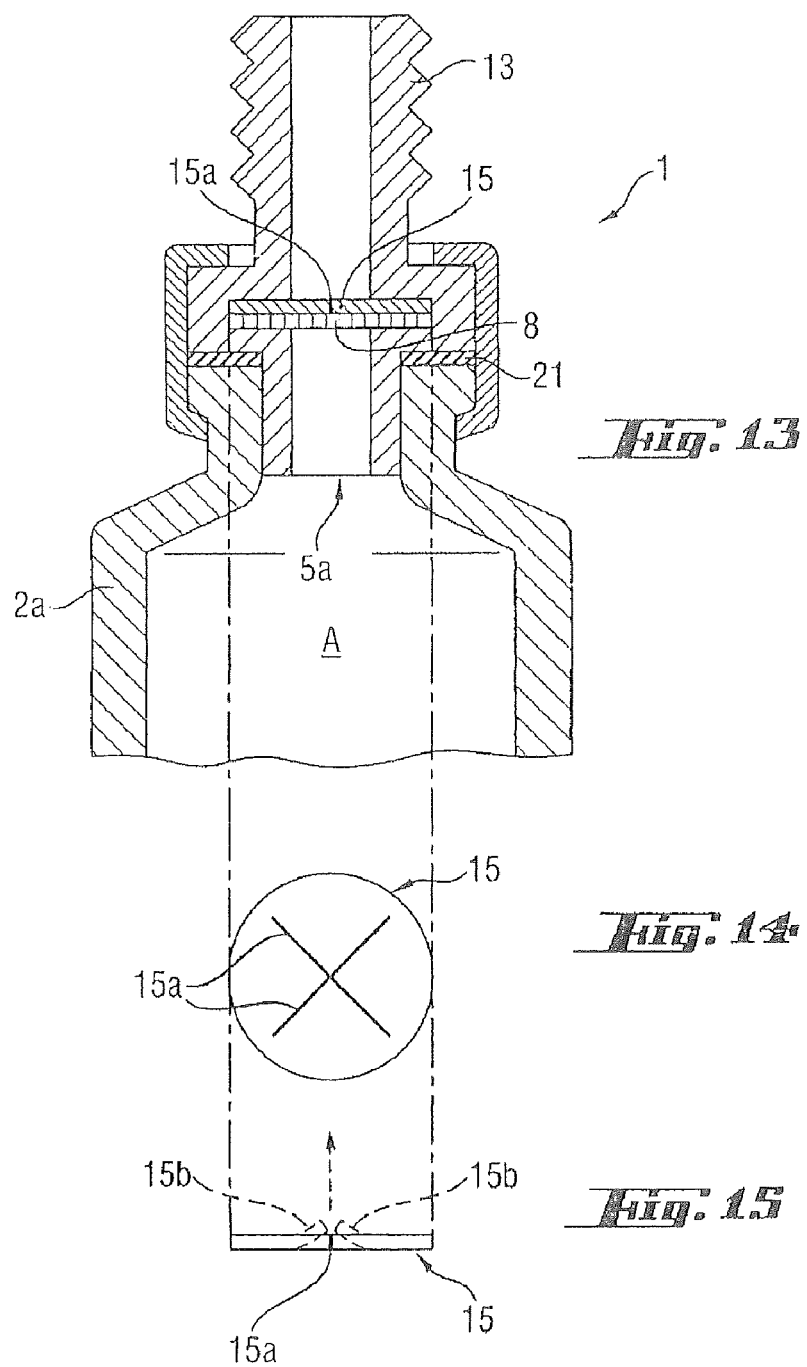

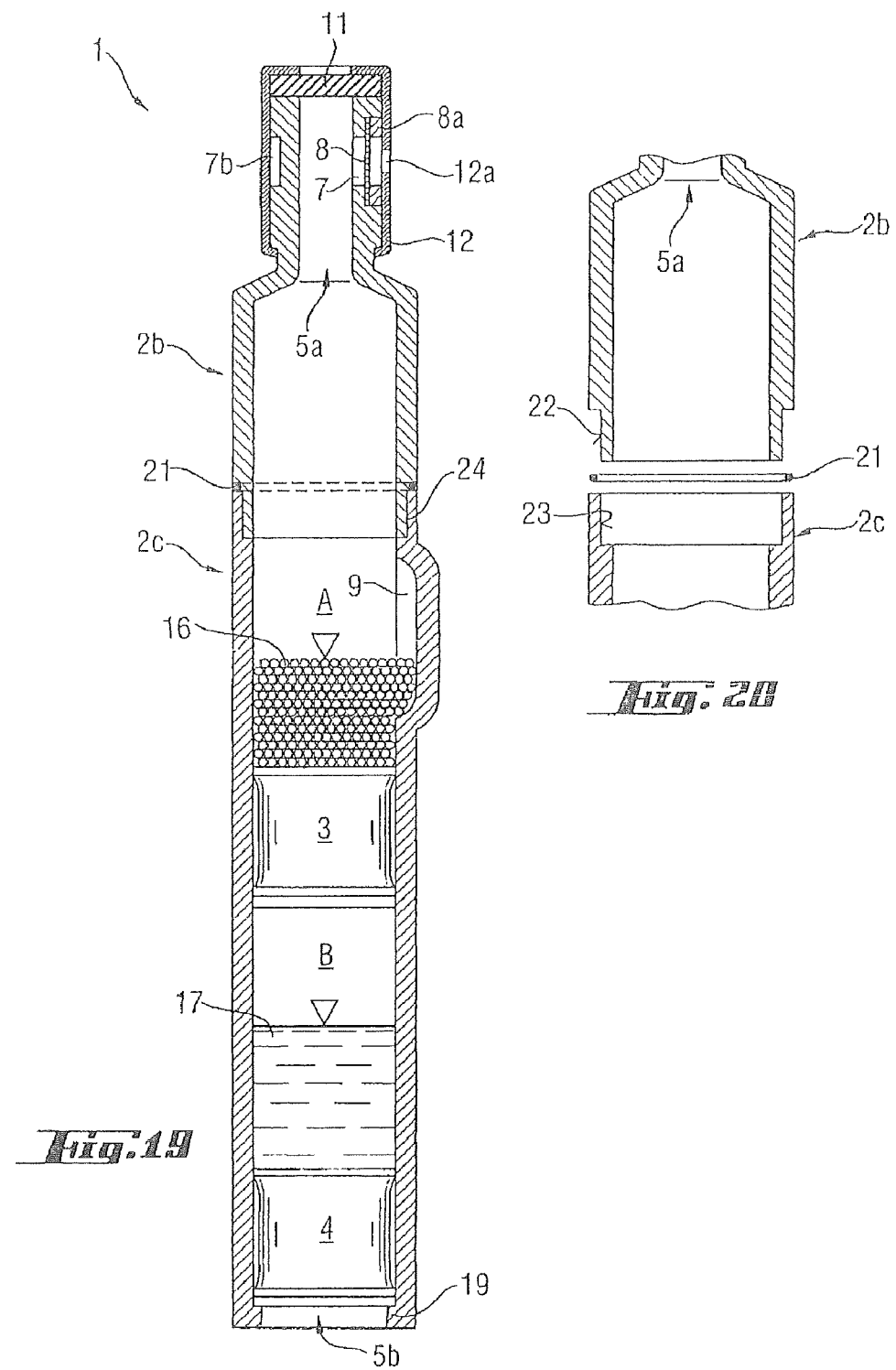

TWO-CHAMBER INJECTION DEVICE HAVING GAS-PERMEABLE MEMBRANE

BACKGROUND

Two-chamber syringes are being developed inter alia as a form of administering medical preparations when individual components of the preparation are only stable for a short time for the application when they are mixed with one another, and therefore must be separated from one another for the time period of lengthy storage. A widely encountered example of this is that of freeze-dried preparations, in which active substances sensitive to hydrolysis are separated from the solvent for the storage time and are only reconstituted to form the solution directly before the application. In principle, there are two possibilities here for combining the components, on the one hand the liquid/liquid combination and on the other hand the solid/liquid combination. Two-chamber syringe systems have the advantage that the mixing of the two components can take place without decanting into another container and that administering can then be performed directly from the container. In the form of two-chamber carpules, the containers can be inserted into syringe holders or injector systems (pen systems or autoinjector systems) that are provided for them and can possibly be used repeatedly. As a two-chamber syringe, the container is prepared with a molded-on pushrod or a pushrod screwed into the plunger or a plunger rod for advancing the plungers and with or without a fitted injection needle.

For the application, for example parenteral application, syringe devices such as for example disposable syringes or carpules generally first have to be vented. This step is problematic in particular in the case of automatic dispensing from injector systems, since an uncontrolled escape of highly potent pharmaceutical active substances must be avoided.

U.S. Pat. No. 5,971,953 describes a two-chamber syringe with a lower plunger (lower piston), an upper plunger and a cylindrical shaft (tubular member), gas in the mixing chamber being able to escape through a membrane in the lower plunger and an opening in the cylindrical shaft (opening). The two-chamber syringe described in U.S. Pat. No. 5,971,953 has the disadvantage that venting requires a tubular construction (shaft) for carrying away the air trapped in the syringe through the second plunger. The cylindrical shaft required for this extends the length of the syringe construction by at least the distance to be covered within the syringe cylinder. A combination with autoinjectors leads as a result to disadvantageous dimensionings, which are problematic with respect to suitability for marketing. Further disadvantages are the highly complex production and assembly of the two-chamber syringe as a result of the large number of individual components.

DE 102004055870 describes a single-chamber syringe comprising a cylinder element and a plunger device, a fluid-tight, gas-permeable element being arranged in the plunger device and allowing gas that is in the cylinder element to be removed through it when the plunger device is introduced into the cylinder element.

EP 1237596 B1 describes a single-chamber syringe unit comprising a syringe body with a discharge end, a plunger movably arranged within the syringe body and a connecting tube, which has a distal end and a first end, which is connected to the discharge end of the syringe body, the tube having a venting cap with a throughflow preventer, and the throughflow preventer being gas-permeable, but fluid-tight, and can be formed as a membrane or as a shut-off valve (check valve).

The throughflow preventer serves for venting the syringe after filling of the syringe and before connecting of the connection tube to the patient.

WO 2006007592 describes a syringe system with a front chamber for receiving a liquid and a rear air-filled chamber, it being possible for air to be admitted to the rear chamber under sterile conditions by way of a filter membrane and an opening.

U.S. Pat. No. 4,373,535 describes a single-chamber syringe for the removal of blood samples, comprising a suitable syringe body and a plunger device, the plunger device containing a gas-permeable, but liquid-tight membrane, which serves for venting. The membrane used in U.S. Pat. No. 4,373,535 consists of a gas-permeable paper, which on contact with blood swells and stops further flow of blood. As in the single-chamber syringe described in DE 102004055870, the arrangement of a gas-permeable membrane in the plunger is not expedient for dual-chamber syringes, since here the storage stability is problematic in lengthy storage on account of gas permeation between the two chambers and from the rear chamber into the surroundings. The use of paper membranes is also not suitable as a barrier for maintaining a sterile state throughout the storage time.

SUMMARY

The object of the present invention is therefore to provide an improved syringe device, in particular a two-chamber syringe device, which allows simplified venting.

The invention relates to a two-chamber syringe device comprising a) a cylinder element (2) with a distal outlet opening (5a), a proximal opening (5b) and one or more transfer channels (9), b) a closure element (6) of the distal outlet opening (5a) comprising a sealing disk (11) and a fixing sleeve (12), and c) a distal plunger (3) and a proximal plunger (4), which can be introduced into the cylinder element (2), wherein one or more fluid-tight, gas-permeable membranes (8) are arranged in the wall of the cylinder element (2) or in the closure element (6), allowing gas in the chambers to escape when the plungers (3) and (4) are displaced in the distal direction.

The closure element (6) also optionally comprises an element for fastening a needle, a spacer ring (10), which is positioned between the sealing element and the cylinder element (2), and a sealing ring (21), which is positioned between the spacer ring (10) and the cylinder element (2).

The two-chamber syringe device also optionally comprises a protective cap (14) for fitting onto the distal end of the cylinder element (2) and/or the distal end of the closure element (6).

Inside the cylinder element (2), a chamber A is formed between the closure element (6) and the distal plunger (3) and a chamber B is formed between the distal plunger (3) and the proximal plunger (4).

"Distal" means the end of the respective component of the two-chamber syringe device that is facing the outlet opening (5a) in the assembled state. "Proximal" means the end opposite from the respective distal end.

Preferably, the fluid-tight, gas-permeable membrane (8) is arranged at the distal (needle-side) end of the cylinder element (2) in the region of the chamber A. With further preference, the fluid-tight, gas-permeable membrane (8) is arranged in the closure element (6).

The two-chamber syringe device is suitable as a primary packaging means for a medicament comprising two components, chamber A containing a liquid or solid component, preferably a solid component, and chamber B containing a liquid component. If chamber A contains a solid component, and chamber B contains a liquid component, the fluid-tight, gas-permeable membrane (8) is in particular fluid-tight with respect to the liquid component in the mixture with the solid component. This mixture may be a solution or dispersion (emulsion or suspension). If both chambers A and B contain a liquid component, the fluid-tight, gas-permeable membrane (8) is in particular fluid-tight with respect to the liquid component in chamber A and with respect to the mixture of the two liquid components. The liquid component is a physiologically tolerable solvent, for example water or an aqueous solution, such as for example an aqueous buffer system. The liquid component may contain one or more active substances. If chamber A contains a liquid component, the fluid-tight, gas-permeable membrane (8) is preferably covered during storage by a gas-impermeable protective cap (14), in order to eliminate or significantly reduce losses of liquid by gas permeation through the fluid-tight, gas-permeable membrane (8).

The fluid-tight, gas-permeable membrane (8) may be in direct contact with the product and is consequently a component part of the primary packaging means. To avoid microbial contaminations of the contained medicament over the storage time, sterile filter membranes are preferably used. Particularly preferred are sterile filter membranes with a nominal pore size of less than or equal to 0.2 μm, for example sterile filter membranes of hydrophobic polytetrafluoroethylene (PTFE). The fluid-tight, gas-permeable membrane (8) is a hydrophobic membrane, which allows gas to pass through, but does not allow aqueous liquids, such as the liquid component contained in the two-chamber syringe device according to the invention, to pass through. The membranes can be sterilized by suitable methods (for example radiation sterilization, ethylene oxide sterilization), so that they can be used as a sterile packaging means component. At the same time, membranes of PTFE are largely inert, so that they permit good compatibility with a wide range of different products. For the mechanical stabilizing and fixing of the membrane, supporting elements, for example of polypropylene, may, if required, be applied to one or both sides (PP-reinforced PTFE membrane, not depicted). The membrane is also secured in a frame (8a) in the edge region for improved mechanical stability. The production of such fixed PTFE membranes is known for example from the area of sterile filter production (syringe pre-filters).

The two-chamber syringe device according to the invention may also include a valve element (15), which is arranged over the gas-permeable, liquid-tight membrane (8) in such a way that a positive pressure of gas can pass through the membrane (8) and the valve element (15). The valve element (15) also serves as mechanical protection for the fluid-tight, gas-permeable membrane (8) and as a barrier to the exchange of gas with the atmosphere of the storage surroundings of the product. The valve element (15) is preferably formed as a valve membrane.

In a further embodiment, the fluid-tight, gas-permeable membrane (8) and the valve membrane (15) are arranged above the distal opening (5a). In this embodiment, when an injection needle is attached, the valve membrane and the fluid-tight, gas-permeable membrane (8) are pierced by the needle. Polyolefins (polyethylene, polypropylene, polybutylene, polyisobutylene) and polyhalogenated olefins (for example polytetrafluoroethylene (PTFE), ethylene tetrafluoroethylene (ETFE)), polyvinyl chloride (PVC), ethyl vinyl acetate (EVA), polystyrene (PS) and polyester (PES) (for example polycarbonate (PC)) may be used for example as materials for the valve membrane. Similarly, natural and synthetic elastomers such as rubber, halogenated butyl rubber (chlorinated butyl rubber, brominated butyl rubber), EPDM and silicone elastomers may be used. Various membrane materials may also be combined with one another in the form of two-layered or multi-layered laminates for the adjustment of certain properties (for example water vapor permeability, gas permeability). By suitable incisions (15a) in the membrane, for example punched openings in the form of a cross, a valve function is produced, since a positive pressure applied on one side creates an opening in the membrane along the cut line in the membrane, and as a result positive pressure can escape. In the state of rest, the cut edges in the membrane are closed against one another and form a barrier to unhindered atmospheric exchange of the system. The required pressure difference with respect to the opening of the valve can be set by the choice of material, the membrane dimensions and the shape and size of the cut lines. Further preferred as a valve element (15) is a one-way valve, which only allows gas from the syringe device to pass through. This can be produced for example by the valve element resting directly on the fluid-tight, gas-permeable membrane (8) and consequently not allowing any opening of the valve in the direction of the fluid-tight, gas-permeable membrane (8). In an alternative embodiment, the valve element may be produced as a simple flap valve, in that the valve membrane rests on a peripheral shoulder and, as a result, opening is only possible in one direction of throughflow.

The two-chamber syringe device also includes at least one transfer channel (9), also known as a bypass, which makes it possible during the use of the two-chamber syringe device for a liquid component (17) contained in the proximal chamber to be able to mix with a solid or liquid component contained in the distal chamber during the administering of the medicament, while bypassing the plunger (3) or the plungers (3) and (3a). The bypass can be created by one or more channels, which are located in the material of the wall of the cylinder element (2), i.e. let into or worked into the material of the wall. The bypass may also be formed by appropriate forming of the material of the wall inward (not depicted) or outward. The arrangement may be configured axially or radially deviating from the axial direction. The length of the transfer channel is greater than the length of the plunger (3) or, if an additional plunger (3a) is present, greater than the sum of the lengths of the plungers (3) and (3a), to ensure that the flow passes around the plungers.

The cylinder element (2) may be formed for example from glass, plastic, metal or other materials, preferably from a transparent material such as glass or plastic. With preference, the glass conforms to hydrolytic class 1 as defined by the European Pharmacopeia (Ph. Eur.), which may be clear-transparent or, to achieve light stabilization, colored. The production of the cylinder element (2) from glass takes place with preference from tubing glass. Plastics for forming the cylinder element are, for example, polycarbonates, polyesters, cyclo-olefin copolymers (COC) or cyclo-olefin polymers (COP). Preferably, the cylinder element (2) is injection-molded from plastic in clean-room conditions and then sterilized while hermetically packed.

The closure element (6) comprises at least a sealing disk (11) and a fixing sleeve (12). The fixing sleeve (12) brings about the permanent gas- and fluid-tight connection and the sealing force between the sealing element and the cylinder element (2) and consists for example of aluminum or plastic. The connection may be established by methods known to a person skilled in the art, for example by crimping, flanging, pressing or screwing. As a further component part, the closure element (6) may comprise an element for the fastening of a needle. The element for fastening a needle is preferably a formed threaded part (13), onto which a formed needle part can be screwed. Alternatively, a formed needle part may be fitted onto a correspondingly formed element for fastening a needle. Additional functional component parts, for example those for fixing the two-chamber syringe device in a pen or autoinjector, may be integrated in the closure element. These may be, for example, hooks or straps (not depicted), which, if appropriate, may be molded onto the closure part in the injection-molding process. Further functional component parts according to the invention of the closure element (6) may be one or more fluid-tight, gas-permeable membranes (8) and valve membranes (15), vide supra. Furthermore, the closure element (6) may include a spacer ring (10) and optionally, in addition to the spacer ring (10), a sealing ring (21).

The plungers (3), (3a) and (4), the sealing disk (11) and the sealing ring (21) are made independently of one another of elastic material, for example of natural or synthetic rubber, preferably brominated butyl rubber or chlorinated butyl rubber. Optionally, the plungers are coated with PTFE. As a further possible embodiment, the plungers may be made from thermoplastic materials (for example polyethylene or polypropylene) and their fluid-tight seal with respect to the wall of the cylinder element (2) may be established by means of molded-on lamellae or inserted sealing rings (O-rings) of elastic material, as described above. The plungers are of a preferably cylindrical basic form, but other basic forms corresponding to the inner formation of the cylinder element are also possible. The plungers have both a sealing function and a closing function. The sealing function is preferably ensured by one or more lamellar formations of the cylindrical basic form.

In a further embodiment, the fluid-tight, gas-permeable membrane (8) represents the sealing element, the two-chamber syringe device not having any further sealing disk (11).

The spacer ring (10) preferably consists of a thermoplastic material (for example polyethylene or polypropylene); its fluid-tight sealing with respect to the cylinder element (2) is produced, if appropriate, by means of inserted sealing rings (O-rings) (21) of elastic material. The spacer ring serves as a component into which the membrane (8) and, if appropriate, the valve membrane (15) are inserted, and is fastened on the cylinder element (2) by the fixing sleeve. The spacer ring may be formed in such a way that an element for fastening a needle is present at its distal end.

The use of plastic as the material for the cylinder element additionally ensures the low-cost and precise production of the parts, and also the integration of functional parts such as the membrane (8) or the closure element (6). Furthermore, functional parts that are required for operating a pen or autoinjector system can be molded onto the cylinder element (2) in a simple way by injection-molding processes. The injection-molding process represents a simple production process, with the advantages of easily achievable freedom from particles, freedom from pyrogens, sterility, high dimensional stability and recyclability.

The cylinder element (2) may be formed as one part or two parts. In the one-part embodiment, the cylinder element (2) comprises a cylinder (2a). In the two-part embodiment, the cylinder element (2) comprises a first, distal part-cylinder (2b) and a second, proximal part-cylinder (2c). In the two-part embodiment, the transfer channel (9) may be positioned in the distal part-cylinder or in the proximal part-cylinder.

In a preferred embodiment of a two-part cylinder element (2), at least one part-cylinder, with preference part-cylinder (2b), with particular preference both part-cylinders (2b) and (2c), is/are made from plastic. In a particularly preferred embodiment, the two plastic components are connected to each other by means of a screw connection, a sealing element optionally being inserted between the part-cylinders for sealing purposes. Alternatively, the part-cylinders (2b) and (2c) are with preference connected to each other by means of a plug-in or clamping connection. The sealing of the part-cylinders may take place by welding techniques (for example high-frequency or ultrasonic welding) or by adhesion by means of conventional pharmaceutically acceptable adhesives, a sealing element optionally being inserted between the part-cylinders (2b) and (2c). In a preferred embodiment, the distal part-cylinder (2b) is made from plastic during production in such a way that the functional component of the fluid-tight, gas-permeable membrane (8) is integrated into the region of the outlet opening (5a).

If the transfer channel (9) is positioned in the distal part-cylinder (2b), both part-cylinders (2b) and (2c) consist with preference of plastic and are connected to each other by means of a plug-in, clamping or screw connection, a sealing element optionally being inserted between the part-cylinders for sealing purposes. The first, distal part-cylinder (2b) comprises a plunger (3) at its proximal end. The outlet opening (5a) is closed by a closure element (6). It is especially preferred in this embodiment for the distal end of the second, proximal part-cylinder (2c) to contain an axial groove (18), by way of which the pressure building up in the part-cylinder (2c) during the assembly of the two part-cylinders can escape; alternatively, the proximal plunger (4) may be positioned in the part-cylinder (2c) in such a way that, during assembly, it is displaced into the desired end position at the proximal end by the built-up pressure. Optionally, the part-cylinder (2c) contains a stop (19) at the proximal end. The part-cylinder (2c) may additionally contain a plunger (3a) at its distal end. Inside the cylinder element (2), a chamber A is formed between the closure element (6) and the distal plunger (3) and a chamber B is formed between the plunger (3a) and the proximal plunger (4).

The two-part two-chamber carpule according to the invention has the advantage that the two part-cylinders can be filled separately from each other through the entire diameter of the part-cylinders, and that the first, distal part-cylinder (2b) and, if the plunger (3a) is present, also the second, proximal part-cylinder (2c) can be produced, and consequently kept in storage, separately from each other. The optional intermediate plunger (3a) also has the effect that there is no risk of contamination by the solid or liquid component at the points of contact between the first and second part-cylinders. A further advantage of the two-part embodiment is a maximum opening diameter, corresponding to the overall inside diameter of the cylinder, for filling with solid or liquid components, whereby the production step of filling can be advantageously carried out, in particular in the case of poorly pouring powders. The possibility of direct filling by way of large openings means that lyophilizing of the solid component in chamber A is no longer necessary. Instead, the solid component, preferably in powder form, can be filled in. The innocuous filling with powder also ensures that no influencing of the morphological structure of the powder occurs. The carpule is also distinguished by outstanding cost-effectiveness, since the rapidity of filling and possibly adaptation of the rate of filling of the distal part-cylinder (2b) to that of the filling of the proximal part-cylinder (2c) makes the method for producing and filling the two-chamber carpule advantageous.

In a preferred embodiment, the two-chamber syringe device is formed as a carpule. In this case, the two-chamber carpule can be used in application systems, for example pen or autoinjector systems, the application system also including a needle for piercing the sealing element (11), and a drive mechanism for moving the plunger (4) in the distal direction.

In a further embodiment, the two-chamber syringe device additionally includes a needle fastened to the distal end of the cylinder element and intended for piercing the sealing disk (11), and a device for moving the plunger (4) in the distal direction. For example, such a two-chamber syringe device is formed as a disposable syringe.

"Medicament" denotes a pharmaceutical formulation comprising at least one active, low molecular weight compound having a molecular weight of up to 1500 Da, a pharmaceutical active peptide, protein, DNA, RNA, antibody, enzyme, hormone or oligonucleotide, or a mixture thereof, preferably comprising at least one peptide, more preferably a peptide for treating Diabetes mellitus or complications of Diabetes mellitus such as, for example, diabetic retinopathy, with particular preference human insulin or a human insulin analog or derivative, glucagon-like peptide 1 (GLP1) or an analog or derivative thereof, or exendin-3 or exendin-4 or an analog or derivatives of exendin-3 or exendin-4.

Insulin analogs are, for example, Gly(A21), Arg(B31), Arg (B32)-human insulin; Lys(B3), Glu(B29)-human insulin; Lys (B28), Pro(B29)-human insulin; Asp(B28)-human insulin; human insulin in which proline in position B28 has been substituted by Asp, Lys, Leu, Val or Ala, and where Lys in position B29 may be substituted by Pro; Ala(B26)-human insulin; des(B28-B30)-human insulin; des(B27)-human insulin, and des(B30)-human insulin.

Insulin derivatives are, for example, B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 denotes preferably exendin-4(1-39), a peptide having the sequence H-His-Gly-Glu-Gly-Thr-Phe-Thr-Ser-Asp-Leu-Ser-Lys-Gin-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$.

Exendin-4 derivatives are selected, for example, from the following group of compounds:
H-$(Lys)_4$-des $Pro^{36}$, des $Pro^{37}$ exendin-4(1-39)-$NH_2$,
H-$(Lys)_5$-des $Pro^{36}$, des $Pro^{37}$ exendin-4(1-39)-$NH_2$,
des $Pro^{36}$ [$Asp^{28}$] exendin-4(1-39),
des $Pro^{36}$ [$IsoAsp^{28}$] exendin-4(1-39),
des $Pro^{36}$ [$Met(O)^{14}$, $Asp^{28}$] exendin-4(1-39),
des $Pro^{36}$ [$Met(O)^{14}$, $IsoAsp^{28}$] exendin-4(1-39),
des $Pro^{36}$ [$Trp(O_2)^{25}$, $Asp^{28}$] exendin-4(1-39),
des $Pro^{36}$ [$Trp(O_2)^{25}$, $IsoAsp^{28}$] exendin-4(1-39),
des $Pro^{36}$ [$Met(O)^{14}$ $Trp(O_2)^{25}$, $Asp^{28}$] exendin-4(1-39),
des $Pro^{36}$ [$Met(O)^{14}$ $Trp(O_2)^{25}$, $IsoAsp^{28}$] exendin-4(1-39); or
des $Pro^{36}$ [$Asp^{28}$] exendin-4(1-39),
des $Pro^{36}$ [$IsoAsp^{28}$] exendin-4(1-39),
des $Pro^{36}$ [$Met(O)^{14}$, $Asp^{28}$] exendin-4(1-39),
des $Pro^{36}$ [$Met(O)^{14}$, $IsoAsp^{28}$] exendin-4(1-39),
des $Pro^{36}$ [$Trp(O_2)^{25}$, $Asp^{28}$] exendin-4(1-39),
des $Pro^{36}$ [$Trp(O_2)^{25}$ $IsoAsp^{28}$] exendin-4(1-39),
des $Pro^{36}$ [$Met(O)^{14}$ $Trp(O_2)^{25}$, $Asp^{28}$] exendin-4(1-39),
des $Pro^{36}$ [$Met(O)^{14}$ $Trp(O_2)^{25}$, $IsoAsp^{28}$] exendin-4(1-39), where the group -Lys-$NH_2$ is linked to the C terminus of the exendin-4 derivative; or
an exendin-4 derivative of the sequence
H-$(Lys)_6$-des $Pro^{36}$ [$Asp^{28}$] exendin-4(1-39)-$Lys_6$-$NH_2$,
des $Asp^{28}$ $Pro^{36}$, $Pro^{37}$, Pro38 exendin-4(1-39)-$NH_2$,
H-$(Lys)_6$-des $Pro^{36}$, $Pro^{38}$ [$Asp^{28}$] exendin-4(1-39)-$NH_2$,
H-Asn-$(Glu)_5$-des $Pro^{36}$, $Pro^{37}$, $Pro^{38}$ [$Asp^{28}$] exendin-4(1-39)-$NH_2$,
des $Pro^{36}$, $Pro^{37}$, $Pro^{38}$ [$Asp^{28}$] exendin-4(1-39)-$(Lys)_6$-$NH_2$,
H-$(Lys)_6$-des $Pro^{36}$, $Pro^{37}$, $Pro^{38}$ [$Asp^{28}$] exendin-4(1-39)-$(Lys)_6$-$NH_2$,
H-Asn-$(Glu)_5$-des $Pro^{36}$, $Pro^{37}$, Pro [$Asp^{28}$] exendin-4(1-39)-$(Lys)_6$-$NH_2$,
H-$(Lys)_6$-des $Pro^{36}$ [$Trp(O_2)^{25}$, $Asp^{28}$] exendin-4(1-39)-$Lys_6$-$NH_2$,
H-des $Asp^{28}$ $Pro^{36}$, $Pro^{37}$, $Pro^{38}$ [$Trp(O_2)^{25}$] exendin-4(1-39)-$NH_2$,
H-$(Lys)_6$-des $Pro^{36}$, $Pro^{37}$, $Pro^{38}$ [$Trp(O_2)^{25}$, $Asp^{28}$] exendin-4(1-39)-$NH_2$,
H-Asn-$(Glu)_5$-des $Pro^{36}$, $Pro^{37}$, $Pro^{38}$ [$Trp(O_2)^{25}$, $Asp^{28}$] exendin-4(1-39)-$NH_2$,
des $Pro^{36}$, $Pro^{37}$, $Pro^{38}$ [$Trp(O_2)^{25}$, $Asp^{28}$] exendin-4(1-39)-$(Lys)_6$-$NH_2$,
H-$(Lys)_6$-des $Pro^{36}$, $Pro^{37}$, $Pro^{38}$ [$Trp(O_2)^{25}$, $Asp^{28}$] exendin-4(1-39)-$(Lys)_6$-$NH_2$,
H-Asn-$(Glu)_5$-des $Pro^{36}$, $Pro^{37}$, $Pro^{38}$ [$Trp(O_2)^{25}$, $Asp^{28}$] exendin-4(1-39)-$(Lys)_6$-$NH_2$,
H-$(Lys)_6$-des $Pro^{36}$ [$Met(O)^{14}$, $Asp^{28}$] exendin-4(1-39)-$Lys_6$-$NH_2$,
des $Met(O)^{14}$ $Asp^{28}$ $Pro^{36}$, $Pro^{37}$, $Pro^{38}$ exendin-4(1-39)-$NH_2$,
H-$(Lys)_6$-des $Pro^{36}$, $Pro^{37}$, $Pro^{38}$ [$Met(O)^{14}$, $Asp^{28}$] exendin-4(1-39)-$NH_2$,
H-Asn-$(Glu)_5$-des $Pro^{36}$, $Pro^{37}$, $Pro^{38}$ [$Met(O)^{14}$, $Asp^{28}$] exendin-4(1-39)-$NH_2$,
des $Pro^{36}$, $Pro^{37}$, $Pro^{38}$ [$Met(O)^{14}$, $Asp^{28}$] exendin-4(1-39)-$(Lys)_6$-$NH_2$,
H-$(Lys)_6$-des $Pro^{36}$, $Pro^{37}$, $Pro^{38}$ [$Met(O)^{14}$, $Asp^{28}$] exendin-4(1-39)-$(Lys)_6$-$NH_2$,
H-Asn-$(Glu)_5$ des $Pro^{36}$, $Pro^{37}$, $Pro^{38}$ [$Met(O)^{14}$, $Asp^{28}$] exendin-4(1-39)-$(Lys)_6$-$NH_2$,
H-$Lys_6$-des $Pro^{36}$ [$Met(O)^{14}$, $Trp(O_2)^{25}$, $Asp^{28}$] exendin-4(1-39)-$Lys_6$-$NH_2$,
H-des $Asp^{28}$ $Pro^{36}$, $Pro^{37}$, $Pro^{38}$ [$Met(O)^{14}$, $Trp(O_2)^{25}$] exendin-4(1-39)-$NH_2$,
H-$(Lys)_6$-des $Pro^{36}$, $Pro^{37}$, $Pro^{38}$ [$Met(O)^{14}$, $Asp^{28}$] exendin-4(1-39)-$NH_2$,
H-Asn-$(Glu)_5$-des $Pro^{36}$, $Pro^{37}$, $Pro^{38}$ [$Met(O)^{14}$, $Trp(O_2)^{25}$, $Asp^{28}$] exendin-4(1-39)-$NH_2$
des $Pro^{36}$, $Pro^{37}$, $Pro^{38}$ [$Met(O)^{14}$, $Trp(O_2)^{25}$, $Asp^{28}$] exendin-4(1-39)-$(Lys)_6$-$NH_2$,
H-$(Lys)_6$-des $Pro^{36}$, $Pro^{37}$, $Pro^{38}$ [$Met(O)^{14}$, $Trp(O_2)^{25}$, $Asp^{28}$] exendin-4(S1-39)-$(Lys)_6$-$NH_2$,
H-Asn-$(Glu)_5$-des $Pro^{36}$, $Pro^{37}$, $Pro^{38}$ [$Met(O)^{14}$, $Trp(O_2)^{25}$, $Asp^{28}$] exendin-4(1-39)-$(Lys)_6$-$NH_2$;
or a pharmaceutically acceptable salt or solvate of one of the aforementioned exendin-4 derivatives.

Hormones are preferably hypophysial hormones or hypothalamic hormones or peptides with regulatory activity, and also antagonists thereof, in accordance with the publication Rote Liste, 2008 edition, section 50. Examples of hormones are gonadotropin (follitropin, lutropin, chorionic gonadotropin, menotropin), somatropin, desmopressin, terlipressin, gonadorelin, triptorelin, leuprorelin, buserelin, nafarelin, goserelin.

Pharmaceutically acceptable salts are, for example, acid addition salts and basic salts. Acid addition salts are, for example, HCl or HBr addition salts. Basic salts are, for example, salts in which the cation is selected from the group alkali metal salts, Na$^+$ or K$^+$ for example, or alkaline earth metal salts, Ca$^{2+}$ for example, or ammonium ions N$^+$(R$_1$)(R$_2$)(R$_3$)(R$_4$), where R$_1$ to R$_4$ independently of one another have the following definitions:

hydrogen, optionally substituted $C_1$-$C_6$ alkyl, optionally substituted $C_2$-$C_6$ alkenyl, optionally substituted $C_6$-$C_{10}$ aryl, or optionally substituted $C_6$-$C_{10}$ heteroaryl. Further examples of pharmaceutically acceptable salts are described in "Remington's Pharmaceutical Sciences" 17th edn., Alfonso R. Gennaro (ed.), Mark Publishing Company, Easton, Pa., U.S.A., 1985, and in Encyclopedia of Pharmaceutical Technology.

Pharmaceutically acceptable solvates are, for example, hydrates.

It is common to all the embodiments that the liquid component and the solid component are filled with preference under aseptic conditions. Given adequate stability of the product, treatment with ionizing rays may possibly follow to additionally ensure sterility.

To avoid environmental effects and unintended contamination during storage, the two-chamber syringe device may also be provided with an outer packaging. If necessary to achieve adequate storage stability, the outer packaging may be produced with preference from sheet materials that represent a gas barrier. Such gas-tight sheet materials are, for example, aluminum foils, plastic-laminated aluminum foils or aluminum-coated plastic films. Further suitable sheets are plastic films of monomaterials or laminated plastic films comprising two or more layers, which, depending on their sheet thickness and composition, may likewise represent good gas barriers. The sheet materials that come into consideration for this are known to a person skilled in the art of packaging technology and are characterized by their gas and water vapor permeability characteristics.

For the use according to the invention, the user may be provided with all the required components in one pack as a kit of parts. Apart from the two-chamber syringe device as a carpule, disposable syringe, pen or autoinjector, this kit additionally contains needles for attachment, and optionally one or more disinfection pads for disinfecting the surface of the closure element (6) before the needle is attached and for disinfecting the puncture site on the skin.

The two-chamber syringe device according to the invention has the advantage that it provides a simple and very low-cost solution for removing gaseous medium that is in the syringe device from the syringe cylinder. Venting by means of a needle is avoided. The patient is consequently no longer faced with the risk of having to place a needle onto a system under pressure and thereby become unwantedly contaminated with a highly potent medicament. When the application system is used over a lengthy period of time or stored over a lengthy period of time, gas that was previously dissolved in the liquid component can become separated from the liquid component, for example by heating of the medicament. This possibly necessitates renewed venting, which is simplified by the two-chamber syringe system according to the invention.

The two-chamber syringe device according to the invention can also be used in automatic applicators, it likewise being possible for the venting step to be performed automatically.

The two-chamber syringe device according to the invention may, for example, be used as follows: firstly, in a mixing step, the plunger (4) is moved in the distal direction, whereby, with a simultaneous advancement of the plunger (3), the content of the chamber B is transferred via the bypass (9) into the chamber A and mixed. At the same time, gas contained in the two-chamber syringe device can already escape through the fluid-tight, gas-permeable membrane (8), since the advancement of the plungers (3) and (4) causes the volume inside the two-chamber syringe device to be reduced, and consequently a positive pressure to be produced in the system by compression of the gas. In the subsequent venting step (priming), the plungers (3) and (4) are jointly moved in the distal direction, a pressure being built up in the device. The pressure can escape from the system before a needle is attached, as soon as the orientation of the fluid-tight, gas-permeable membrane (8) coincides with the orientation of the gas in chamber A. If, for example, the sealing disk (11) is formed as the fluid-tight, gas-permeable membrane (8), gas can escape when the two-chamber syringe device is put in the upright position (with the closure element upward). The orientation of the syringe device does not necessarily have to be correct when the plunger (4) is moved in the distal direction, but venting should be performed before the needle is attached. In the attachment of the needle, in which the sealing element is pierced, the two-chamber syringe device then no longer contains compressed gas. If no further advancing pressure is produced by the plunger, there is therefore no risk of the user being contaminated by medicament escaping in an uncontrolled manner or of medicament being lost.

In general, a combination of all the stated general and preferred features of the embodiments is technically possible.

Further refinements and advantages of the invention emerge from the following description of the exemplary embodiments that are represented in the drawings.

BRIEF DESCRIPTION OF THE DRAWINGS

FIG. 1 shows a cross-sectional longitudinal view of one embodiment of the present invention;

FIG. 2 shows an enlarged cross-sectional transverse view of one portion of the wall of the embodiment shown in FIG. 1;

FIG. 3 shows an enlarged cross-sectional longitudinal view of one portion of the wall of the embodiment shown in FIG. 1;

FIG. 5 shows a cross-sectional longitudinal view of a third embodiment of the present invention;

FIG. 6 shows a cross-sectional longitudinal view of a fourth embodiment of the present invention;

FIG. 7 shows a cross-sectional longitudinal view of fifth embodiment of the present invention;

FIG. 8 shows an enlarged cross-sectional longitudinal view of one portion of the wall of the embodiment shown in FIG. 7;

FIG. 9 shows a cross-sectional longitudinal view of a sixth embodiment of the present invention;

FIG. 12 shows a cross-sectional longitudinal view of an eight embodiment of the present invention;

FIG. 13 shows a close-up cross-sectional longitudinal view of the distal end of the embodiment illustrated in FIG. 12;

FIG. 14 shows an enlarged cross-sectional transverse view of one portion of the distal end of the embodiment shown in FIG. 12;

FIG. 15 shows an enlarged cross-sectional view of one portion of the embodiment shown in FIG. 14;

FIG. 19 shows a cross-sectional longitudinal view of an eleventh embodiment of the present invention; and FIG. 20 shows a close-up cross-sectional longitudinal view of the distal end of the embodiment illustrated in FIG. 19.

DETAILED DESCRIPTION

Example 1

Figure 4:
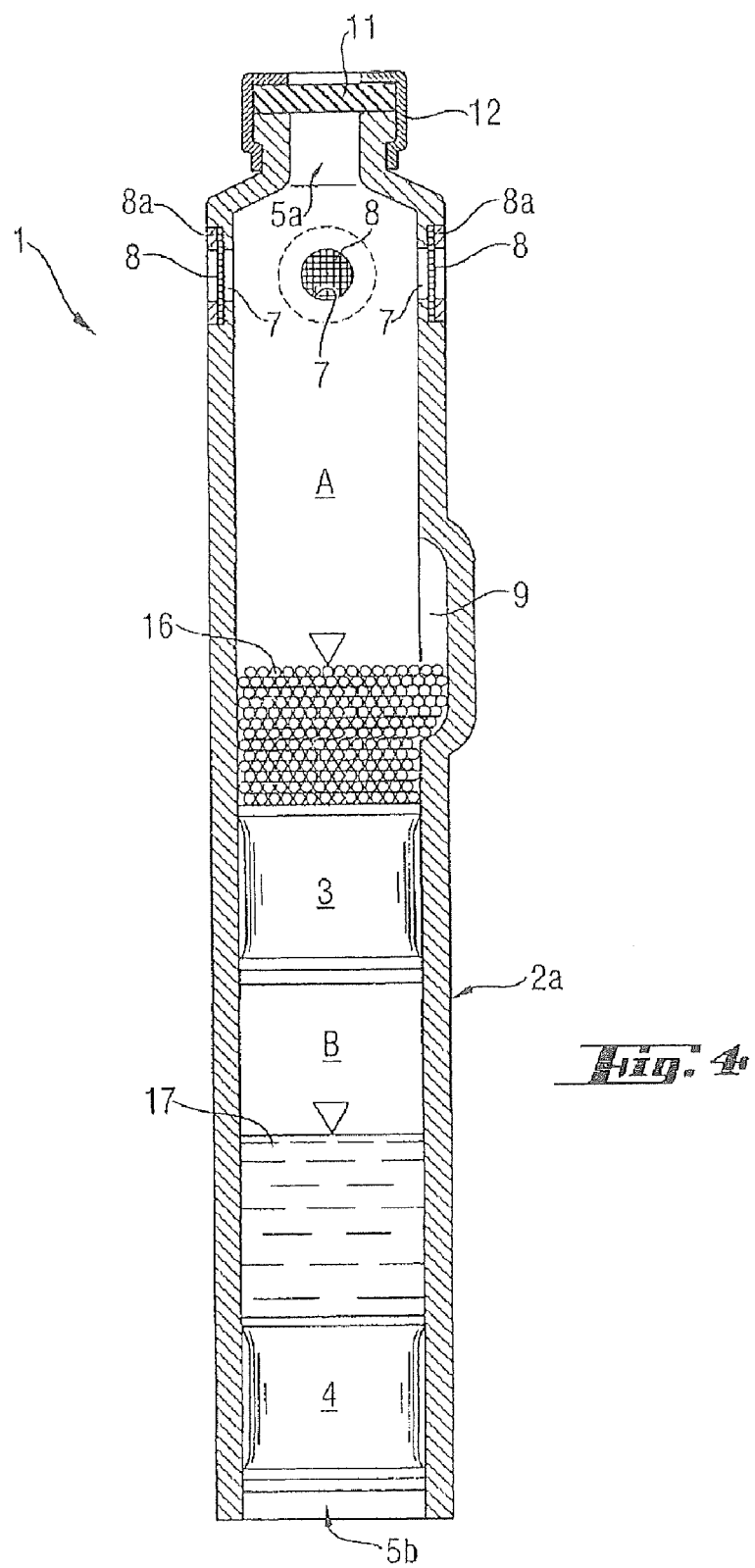
FIG. 4 shows a cross-sectional longitudinal view of a second embodiment of the present invention.

A two-chamber syringe device (1) according to a first exemplary embodiment of the invention is described below with reference to FIGS. 1 to 3.

As shown in FIG. 1, the two-chamber syringe device (1) comprises a cylinder element (2) made up of a cylinder (2a), two plungers (3) and (4) and a closure element (6, numeral not depicted). The cylinder element (2) has an outlet opening (5a) and, at the proximal end, a large opening (5b), into which the plungers (3) and (4) are introduced. The outlet opening (5a) is closed by a closure element (6). Between the closure element (6) and the plunger (3), and bounded by the wall of the cylinder (2a), a chamber A is created. Between the plunger (3) and the plunger (4), and bounded by the wall of the cylinder (2a), a chamber B is created. A bore (7) is provided in the wall of the cylinder (2a), in the region of the chamber A below the shoulder at the distal end. The bore (7) is closed by a fluid-tight, gas-permeable membrane (8). In production engineering terms, this is possible, for example, by the wall in the region of the bore (7) forming an abutment or a shoulder (7a), in which the membrane is placed and welded by means of a frame (8a). A transfer channel (9) is also formed in the wall of the cylinder (2a) in the region of the chamber A and near the distal end of the plunger (3). In this example, the closure element (6) comprises a sealing disk (11) and a fixing sleeve (12). The sealing disk (11) is placed onto the outlet opening (5a) and is enclosed by the fixing sleeve (12) and firmly connected to the cylinder (2a) by flanging.

The assembly, filling and use of the two-chamber syringe device (1) according to the invention is in this case as follows: firstly, the plunger (3) is introduced through the rear opening (5b) into the cylinder (2a) and positioned. Then, the chamber B is filled with the liquid medium through the opening (5b). After that, the plunger (4) is introduced into the opening (5b) and the chamber B is thereby closed. The components are turned through 180 degrees and chamber A is filled with a solid or liquid medium through the outlet opening (5a). After that, the outlet opening (5a) is closed by the closure element (6). In preparation for use, the plunger (4) is pushed in the direction of the outlet opening (5a) by an attached piston rod (not depicted). Since the fluid in chamber B is incompressible, at the same time the plunger (3) is set in a displacing motion. As this happens, the air in chamber A can escape through the fluid-tight, gas-permeable membrane (8), so that no positive pressure is produced in chamber A. The two-chamber syringe device is in this case held in an approximately horizontal position such that the bore (7) is at the uppermost position. When the plunger (3) has reached the region of the formed-in transfer channel (9) by the advancing movement, the fluid can enter the chamber A from chamber B through the transfer channel (9) and mix with the solid or liquid medium in chamber A. At the same time, trapped air can escape by way of the membrane (8). When plunger (4) is in contact with plunger (3), the transfer of the medium from chamber B is ended and the contents of the chambers A and B can be homogeneously mixed. Subsequently, both plungers (3) and (4) are jointly advanced further until the air has been displaced from the chamber A by way of the membrane (8). Since the membrane (8) is only permeable with respect to gas, but not with respect to the liquid, no further advancement of the plungers (3) and (4) is possible. The two-chamber syringe device has then been prepared for the application of the medium. For the application, an application needle is then attached to the closure element (6) in the conventional way and the sealing disk (11) is pierced.

Example 2

A two-chamber syringe device (1) according to a second exemplary embodiment of the invention is described below with reference to FIG. 4. The same parts are in this case denoted by the same designations as in the first exemplary embodiment. As can be seen in the schematic view of FIG. 4, the two-chamber syringe device (1) comprises a cylinder element (2) made up of a cylinder (2a), two plungers (3) and (4) and a closure element (6, numeral not depicted). As a difference from the first exemplary embodiment, formed in the cylinder element (2) on the circumference of the cylinder (2a) in the region of the chamber A below the shoulder at the distal end, are four bores (7), which are respectively closed by a fluid-tight, gas-permeable membrane (8). This allows the closed two-chamber syringe device to be vented in a largely horizontal position and virtually irrespective of an alignment of the cylinder element (2), since there are a number of openings (7), closed by a gas-permeable membrane (8), and the gas in the two-chamber syringe device (1) tends to flow in the direction of the openings (7) when the two-chamber syringe device (1) is held with the outlet opening (5a) raised. Otherwise, the second exemplary embodiment corresponds to the first exemplary embodiment, so you are referred to the description given there.

Example 3

A two-chamber syringe device (1) according to a third exemplary embodiment of the invention is described below with reference to FIG. 5. As can be seen in the schematic sectional view of FIG. 5, the two-chamber syringe device (1) likewise comprises a cylinder element (2) made up of a cylinder (2a), two plungers (3) and (4) and a closure element (6, numeral not depicted). The fluid-tight, gas-permeable membrane (8) is located laterally in the closure element (6). The closure element (6) comprises a spacer ring (10), a sealing disk (11) and a fixing sleeve (12), the bore (7) being formed in the spacer ring (10) and closed by a fluid-tight, gas-permeable membrane (8), which is fixed by a frame (8a). The spacer ring (10) has been fitted onto the cylinder (2a) above the outlet opening (5a). The sealing disk (11) has been placed onto the spacer ring (10). The spacer ring (10) and the sealing disk (11) are enclosed by the fixing sleeve (12) and firmly connected to the cylinder (2a) by flanging. A further sealing ring (21) is inserted between the cylinder (2a) and the spacer ring (10) (as depicted). The sealing ring (21) may be omitted if adequately elastic material is used for the spacer ring (10). To facilitate the venting, a peripheral venting channel (7b) has been formed in the spacer ring (10) on the outer side at the level of the bore (7). At the same level there is a bore (12a) in the fixing sleeve (12), which bore makes it possible for the air to escape. By analogy with exemplary embodiment 2, it is also possible for a number of bores (7), which are respectively closed by fluid-tight, gas-permeable membranes, to be arranged on the circumference of the spacer ring. As a result, the closed two-chamber syringe device can be vented in the vertical position, since the bore (7), closed by the gas-permeable membrane, is provided in the direct vicinity of the outlet opening and the gas in the two-chamber syringe device (1) tends to flow in the direction of the opening when the two-chamber syringe device (1) is held with the outlet opening (5a) upward. Otherwise, the third exemplary embodiment corresponds to the first exemplary embodiment, so you are referred to the description given there.

Example 4

A two-chamber syringe device (1) according to a further exemplary embodiment of the invention is described below with reference to FIG. 6. As can be seen in the schematic sectional view of FIG. 6, the two-chamber syringe device (1) comprises a cylinder element (2) made up of a cylinder (2a), two plungers (3) and (4) and a closure element (6, numeral not depicted). The fluid-tight, gas-permeable membrane (8) is located laterally near the outlet opening (5a) in the wall of the cylinder (2a). The closure element (6) comprises a sealing disk (11) and a fixing sleeve (12). The bore (7) is formed in the cylinder (2a) in the region of the fixing sleeve and is closed by a fluid-tight, gas-permeable membrane (8). The sealing disk (11) has been fitted onto the outlet opening (5a) and is enclosed by the fixing sleeve (12) and firmly connected to the cylinder (2a) by flanging. To facilitate the venting, a peripheral venting channel (7b) has been formed in the cylinder (2a) on the outer side at the level of the bore (7). At the same level there is a bore (7) in the fixing sleeve (12), which bore makes it possible for the air to escape from the interior of the cylinder. By analogy with exemplary embodiment 2, it is also possible for a number of bores (7), which are respectively closed by fluid-tight, gas-permeable membranes, to be arranged on the circumference of the cylinder (2a). As a result, the closed two-chamber syringe device can be vented in the vertical position, since the bore (7), closed by the fluid-tight gas-permeable membrane (8), is provided in the direct vicinity of the outlet opening (5a) and the gas in the two-chamber syringe device (1) tends to flow in the direction of the opening when the two-chamber syringe device (1) is held with the outlet opening (5a) upward. Otherwise, the exemplary embodiment corresponds to the first exemplary embodiment, so you are referred to the description given there.

Example 5

A two-chamber syringe device (1) according to a further exemplary embodiment of the invention is described below with reference to FIGS. 7 and 8. As can be seen in the schematic sectional view of FIG. 7, the two-chamber syringe device (1) comprises a two-part cylinder element (2) made up of the part-cylinders (2b) and (2c), two plungers (3) and (4), and a closure element (6), in which the opening (12a) in the fixing sleeve (12) is arranged opposite the membrane (8) and gas is led away via the venting channel (7b). The part-cylinders are connected to each other by means of a screw connection (FIG. 8). A sealing ring (21), which is inserted between the part-cylinders, is used for sealing purposes. The proximal end of the part-cylinder (2b) terminates at least with the proximal end of the plunger (3). Above the distal end of the plunger (3), part-cylinder (2b) includes a bypass (9) in the region of the chamber A. Otherwise, this exemplary embodiment corresponds to the exemplary embodiment 4, and so you are referred to the description given there.

Example 6

A two-chamber syringe device (1) according to a further exemplary embodiment of the invention is described below with reference to FIG. 9. As can be seen in the schematic sectional view of FIG. 9, the two-chamber syringe device (1) comprises a cylinder element (2) made up of a cylinder (2a), two plungers (3) and (4) and a closure element (6, numeral not depicted). The fluid-tight, gas-permeable membrane (8) is arranged axially in the closure element (6). The closure element (6) comprises a fluid-tight, gas-permeable membrane (8) and a fixing sleeve (12). The fluid-tight, gas-permeable membrane (8) has been fitted onto the outlet opening (5a). The fluid-tight, gas-permeable membrane (8) is secured in an orifice plate (8b) and the orifice plate with the membrane is enclosed by the fixing sleeve (12) and firmly connected to the cylinder (2a) by flanging. In the present example, the transition between the orifice plate (8b) and the cylinder (2a) is sealed by a sealing ring (21). Alternatively, the sealing ring may also be omitted if an elastic material is used for the orifice plate, for example a material described for the plungers (3) and (4) or the sealing disk (11), vide supra.

The positioning of the membrane allows the closed two-chamber syringe device to be completely vented in the vertical position, since the opening that is closed by the fluid-tight, gas-permeable membrane (8) at the same time represents the outlet opening and the gas in the two-chamber syringe device (1) tends to flow in the direction of the opening when the two-chamber syringe device (1) is held with the outlet opening (5a) upward. Otherwise, the fourth exemplary embodiment corresponds to the first exemplary embodiment, so you are referred to the description given there.

Example 7

A two-chamber syringe device (1) according to a further exemplary embodiment of the invention is described below with reference to FIGS. 10 and 11. As can be seen in the schematic sectional view of FIGS. 10 and 11, the two-chamber syringe device (1) comprises a cylinder element (2) made up of a cylinder (2a), two plungers (3) and (4) and a closure element (6, numeral not depicted). The closure element (6) comprises a fixing sleeve (12), a formed threaded part (13), in which a fluid-tight, gas-permeable membrane (8) is fixed, and optionally a protective cap (14). The formed threaded part (13) with the integrated fluid-tight, gas-permeable membrane (8) is fitted onto the outlet opening (5a). The formed threaded part (13) is firmly connected to the fixing sleeve (12) by flanging with the cylinder (2a), the transition between the formed threaded part (13) and the cylinder (2a) being additionally sealed by a sealing ring (21). The formed threaded part (13) is preferably closed by a removable protective cap (14) and allows an injection needle to be screwed on after removal of the protective cap (14). This allows the closed two-chamber syringe device to be completely vented in the vertical position, since the opening that is closed by the fluid-tight, gas-permeable membrane (8) at the same time represents the outlet opening and the gas in the two-chamber syringe device (1) tends to flow in the direction of the opening when the two-chamber syringe device (1) is held with the outlet opening (5a) upward.

Figure 10:
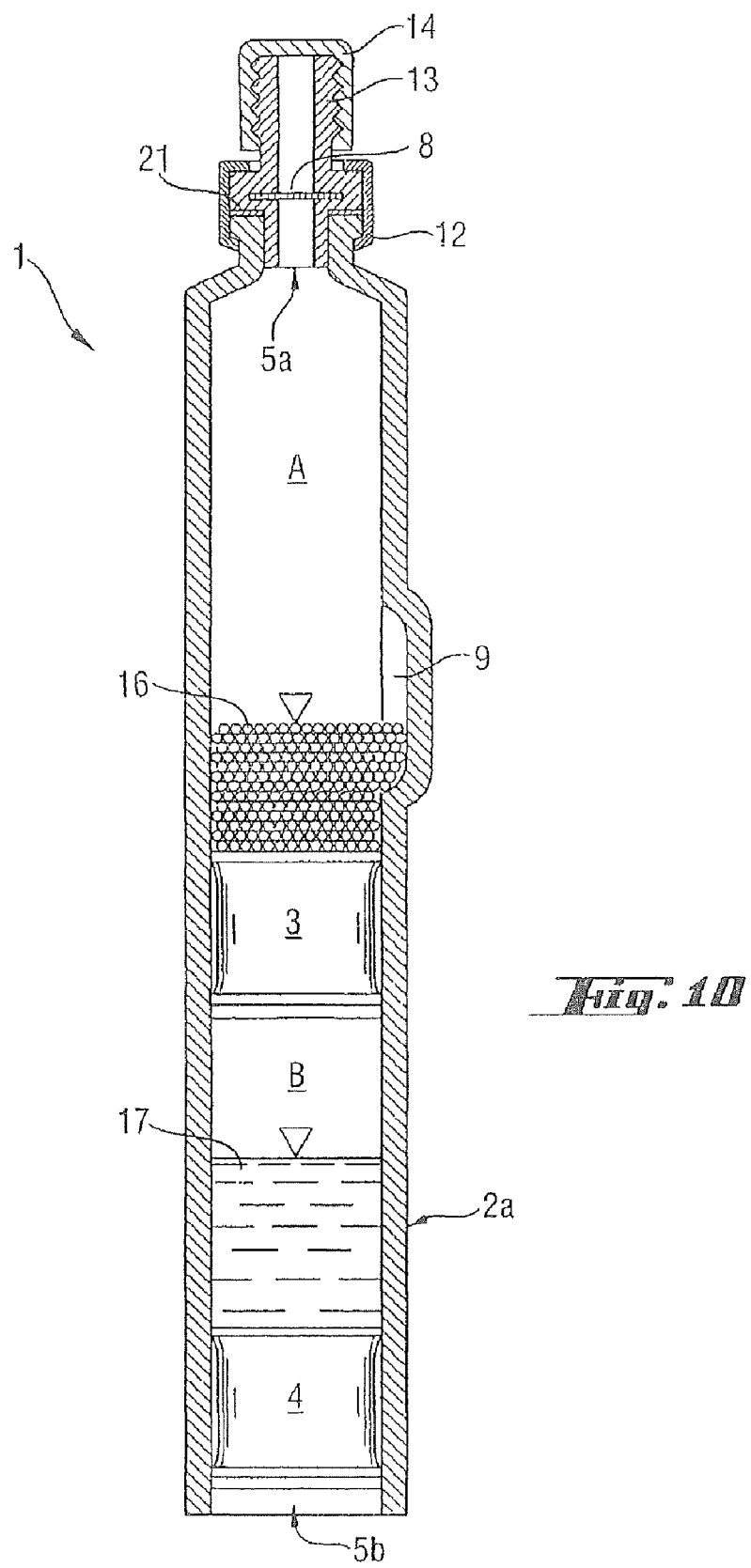
FIG. 10 shows a cross-sectional longitudinal view of a seventh embodiment of the present invention.

In FIG. 10, the membrane (8) is located in the middle of the formed threaded part (13), at a location at which component (13) has its greatest outside diameter. In this way it is possible for example for the membrane (8) to be cast into the formed threaded part (13). For example, the integrated formed threaded part (13) may be produced by placing the membrane (8) onto the distal flange of a proximal part of the formed threaded part and placing the proximal counterpart of the formed threaded part, including the thread and a proximal flange, onto the membrane and the distal flange and fusing it with them (not shown).

Figure 11:
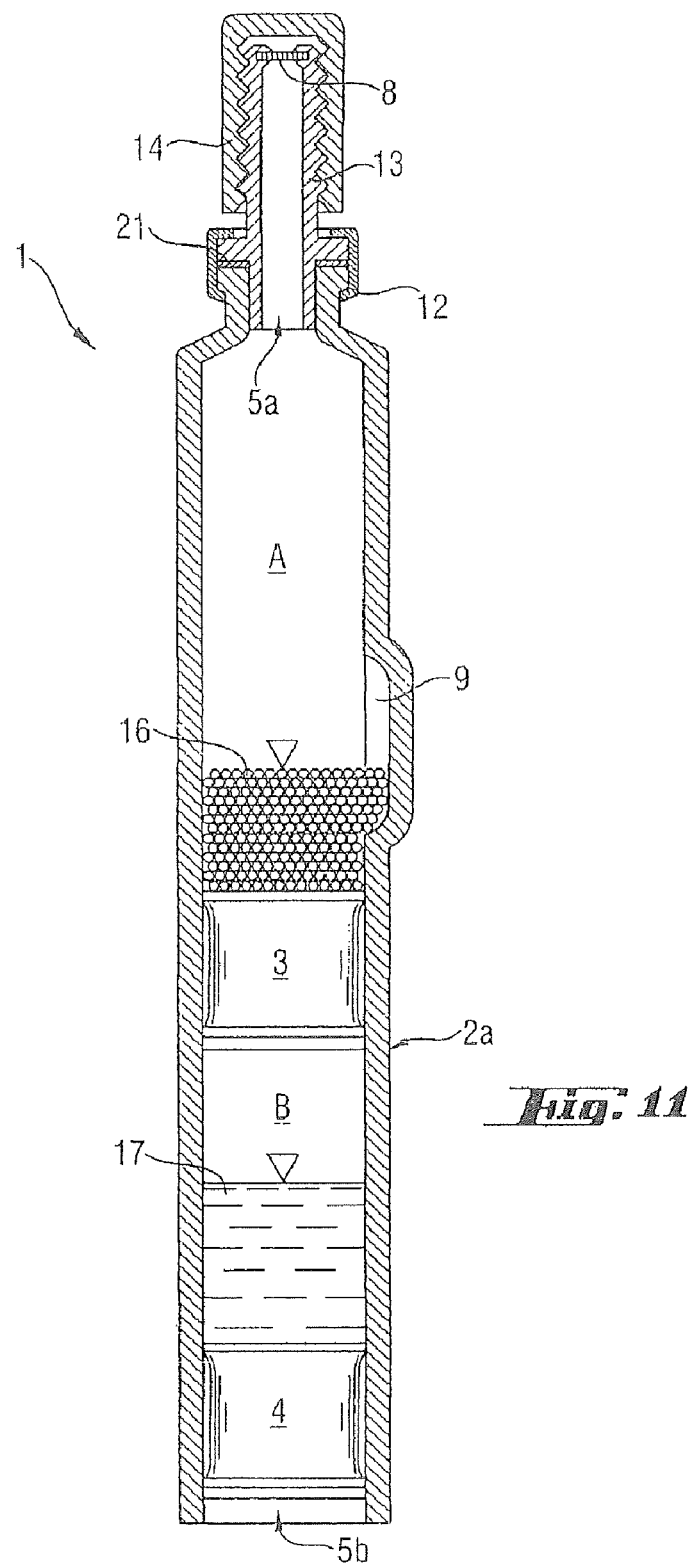
FIG. 11 shows a cross-sectional longitudinal view of the embodiment shown in FIG. 10.

FIG. 11 shows the position of the membrane (8) at the outer end of the formed threaded part (13).

Example 8

A two-chamber syringe device (1), which corresponds to that described in example 7 but with a valve membrane (15) additionally arranged on the outwardly directed side of the membrane (8), is described below with reference to FIGS. 12 to 15. The valve membrane (15) protects the fluid-tight, gas-permeable membrane (8) lying under it and limits the gas diffusion from the storage surroundings into the primary packaging means.

FIG. 13 shows an enlarged detail of the head region of the two-chamber syringe device of this example. FIG. 14 shows a plan view of the valve membrane (15). The valve function is produced by punched lines (15a) made in the form of a cross in the membrane. A positive pressure produced inside the two-chamber syringe device (1) escapes through the gas-permeable membrane (8) by the valve membrane (15) opening along the punched lines (15a). The opened position of the valve membrane when gas passes through is indicated in the side view in FIG. 15 by the position of the opened valve membrane (15b).

Example 9

Figure 16:
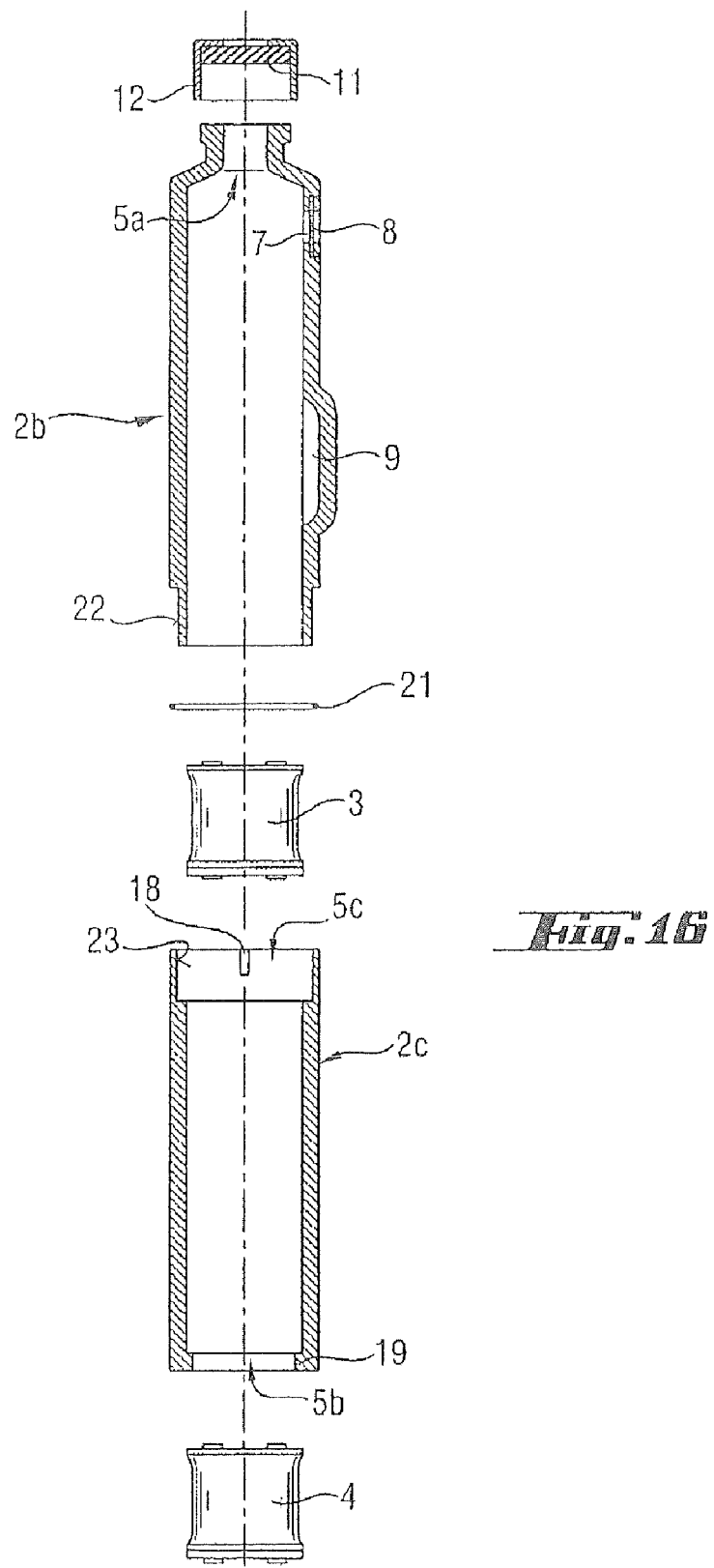
FIG. 16 shows an exploded cross-sectional longitudinal view of a ninth embodiment of the present invention.
Figure 17:
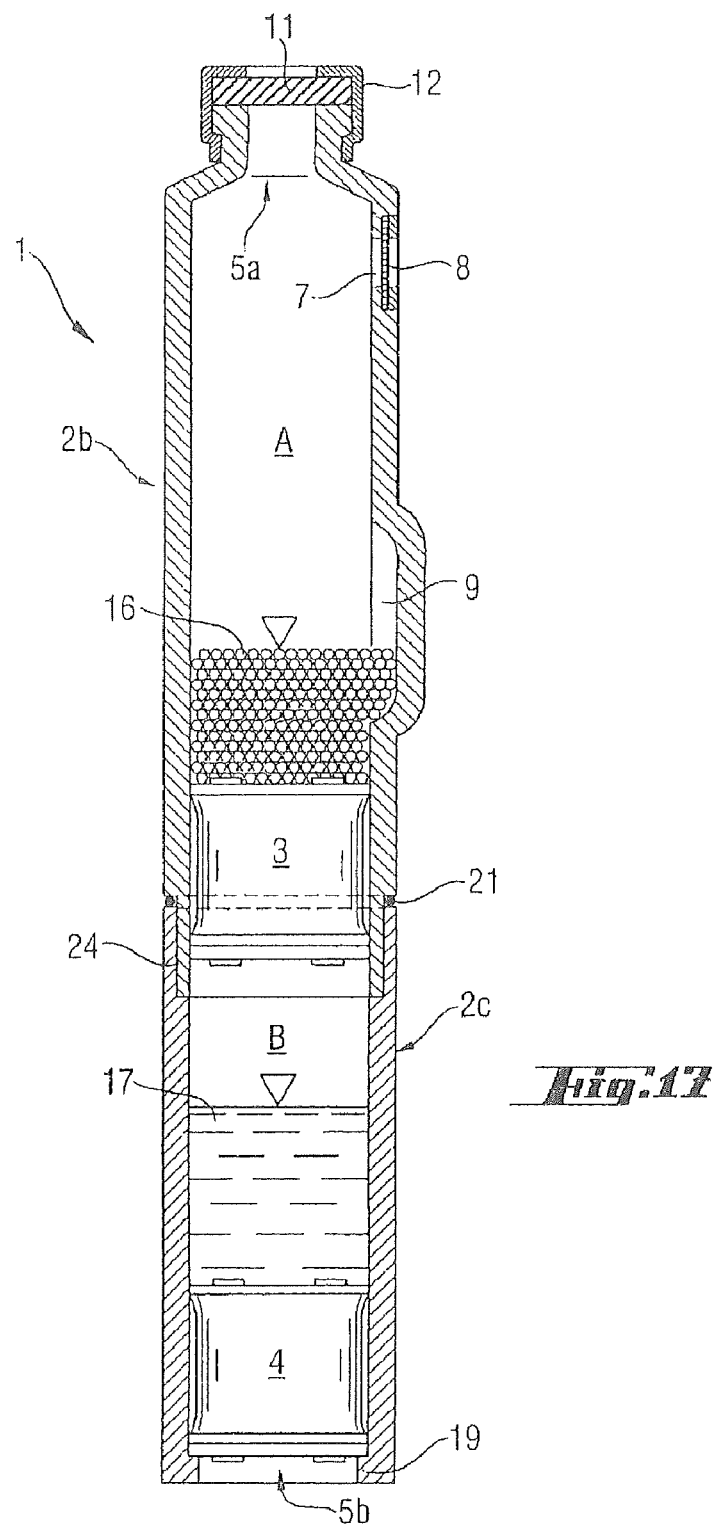
FIG. 17 shows a cross-sectional longitudinal view of the embodiment illustrated in FIG. 16.

A two-chamber syringe device (1) in which the cylinder element (2) is in two parts and comprises a distal part-cylinder (2b) and a proximal part-cylinder (2c), and which also comprises two plungers (3) and (4) and a closure element (6), is described below with reference to FIGS. 16 and 17. The part-cylinders are firmly connected to each other by a plug-in connection at the connecting location (24) and additionally sealed by a sealing ring (21). The fluid-tight, gas-permeable membrane (8) is located laterally below the shoulder region in the vicinity of the distal end of the part-cylinder (2b).

In this embodiment, the bypass (9) is located in the wall of the distal part-cylinder and is dimensioned such that the length of the bypass is greater than the length of the plunger (3).

The proximal part-cylinder (2c) has in the region of the opening (5b) a stop (19), which is intended to prevent the plunger (4) from being forced out by the pressure building up in the chamber B when the part-cylinders (2b) and (2c) are joined together.

In the region of the widening (23) in the part-cylinder (2c) into which the offset (22) in the part-cylinder (2b) is introduced there is an axial groove, which has a length of 50 to 90% of the length of the widening (23) and by way of which the pressure that builds up when the two part-cylinders are joined together is additionally reduced.

You are referred to example 1 for the description of use. FIG. 17 shows the exemplary embodiment in the assembled state with filling of the chambers A (here: solid component) and B (liquid component).

Example 10

Figure 18:
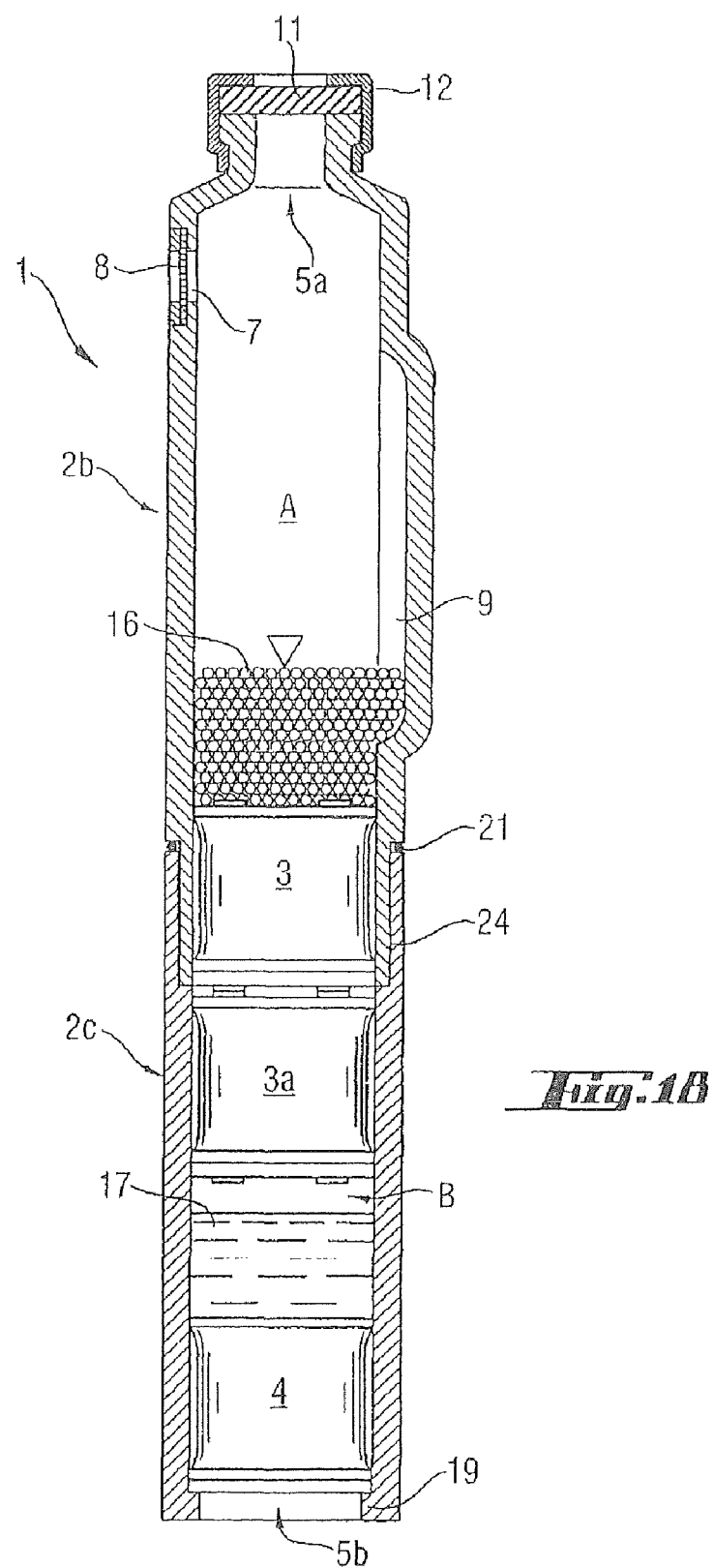
FIG. 18 shows a cross-sectional longitudinal view of a tenth embodiment of the present invention.

A two-chamber syringe device (1) in which the cylinder element (2) is in two parts and comprises a distal part-cylinder (2b) and a proximal part-cylinder (2c), and which also comprises three plungers (3), (3a) and (4) and a closure element (6), is described below with reference to FIG. 18. The part-cylinders are firmly connected to each other by a plug-in connection (24) and additionally sealed by a sealing ring (21). The fluid-tight, gas-permeable membrane (8) is located laterally below the shoulder region in the vicinity of the distal end of the part-cylinder (2b). Preferably, the membrane (8) is positioned on the side opposite from the bypass (9). The exemplary embodiment otherwise corresponds to the two-chamber syringe device given in example 1. FIG. 18 shows the exemplary embodiment in the assembled state with filling of the chambers A (here: solid component) and B.

In this embodiment, the bypass (9) is located in the wall of the distal part-cylinder and is dimensioned such that the length of the bypass is greater than the sum of the lengths of the plungers (3) and (3a).

The proximal part-cylinder (2c) has in the region of the opening (5b) a stop (19), which is intended to prevent the plunger (4) from being forced out by the pressure building up in the chamber B when the plunger (3a) is inserted.

FIG. 18 shows the exemplary embodiment in the assembled state with filling of the chambers A (here: solid component) and B (liquid component).

The assembly and filling of the two-chamber syringe device (1) according to the invention is described below:

For the assembly of the distal part of the two-chamber syringe device, firstly the sealing disk (11) is firmly fixed by means of the fixing sleeve (12) to the distal end of a part-cylinder (2b), into which a gas-permeable, fluid-tight membrane (8) has been worked. Then, a solid component (depicted) or alternatively a liquid component is filled into chamber A through the proximal opening of the part-cylinder (2b), and the proximal opening of the part-cylinder is closed by the plunger (3).

For the assembly of the proximal part of the two-chamber syringe device, firstly the plunger (4) is introduced into the part-cylinder (2c) and positioned at the proximal end of the latter. Then, the chamber B is filled with a liquid medium. Subsequently, the plunger (3a) is introduced into the distal opening of the part-cylinder and chamber B is thereby closed.

Before the two-chamber syringe device is used, the proximal end of the distal part-cylinder (2b) is firmly connected together to the distal end of the proximal part-cylinder (2c), it being possible for the connection to be additionally sealed by a sealing ring (21).

The two part-cylinders (2b) and (2c) can be filled separately from each other and can be stored separately until assembly. This has the advantage that contamination of chamber B with the solid or liquid component in chamber A is avoided. Furthermore, the logistical procedures in industrial-scale production can be planned and implemented more easily. Furthermore, the part-cylinder (2c) can be filled via an opening that is the size of the entire inner diameter of the part-cylinder (2c). This makes the filling of solid components in particular possible in a simplified manner, without filling through the distal outlet opening (5a) and subsequent lyophilizing being necessary.

You are referred to example 1 for the description of use.

Example 11

A further two-chamber syringe device (1), which comprises a two-part cylinder element (2) made up of a distal part-cylinder (2b) and a proximal part-cylinder (2c), two plungers (3) and (4) and a closure element (6, numeral not depicted), is described below with reference to FIGS. 19 and 20. The fluid-tight, gas-permeable membrane (8) is located laterally near the outlet opening (5a) in the wall of the cylinder (2a). The closure element (6) comprises a sealing disk (11) and a fixing sleeve (12). The bore (7) is formed in the part-cylinder (2b) in the region of the fixing sleeve and is closed by a fluid-tight, gas-permeable membrane (8). The sealing disk (11) has been fitted onto the outlet opening (5a) and is enclosed by the fixing sleeve (12) and firmly connected to the part-cylinder (2a) by flanging. To facilitate the venting, a peripheral venting channel (7b) has been formed in (2b) on the outer side at the level of the bore (7). At the same level there is a bore (7) in the fixing sleeve (12), which bore makes it possible for the air to escape from the interior of the cylinder. The bore (7) and the membrane (8) may in this case come to lie one over the other, but with preference the bore (7) and the membrane (8) do not coincide, in order that the membrane (8) is provided with further mechanical protection by the fixing sleeve. By analogy with exemplary embodiment 2, it is also possible for a number of bores (7), which are respectively closed by fluid-tight, gas-permeable membranes, to be arranged on the circumference of the part-cylinder (2b).

FIG. 19 shows the exemplary embodiment in the assembled state with filling of the chambers A (here: solid component) and B. FIG. 20 shows an enlargement of a detail of the connecting location of the two part-cylinders (2b) and (2c).

In this embodiment, the bypass (9) is located in the wall of the proximal part-cylinder (2c) and is dimensioned such that the length of the bypass is greater than the length of the plunger (3).

The proximal part-cylinder (2c) has in the region of the opening (5b) a stop (19), which is intended to prevent the plunger (4) from being forced out by the pressure building up in the chamber B when the plunger (3) is inserted.

The assembly and filling of the two-chamber syringe device (1) according to the invention is described below:

For the assembly of the distal part of the two-chamber syringe device (1), firstly a sealing disk (11) is firmly fixed by means of a fixing sleeve (12) to the distal end of a part-cylinder (2b), into which a gas-permeable, fluid-tight membrane (8) has been worked.

For the assembly of the proximal part of the two-chamber syringe device, firstly the plunger (4) is introduced into the part-cylinder (2c) and positioned at the proximal end of the latter. Then, the chamber B is filled with a liquid medium. Subsequently, the plunger (3) is introduced through the distal opening of the part-cylinder and chamber B is thereby closed. Then, a solid component (depicted) or a liquid component is filled into chamber A through the distal opening of the part-cylinder (2c), and the distal opening is closed by attaching the preassembled distal part of the two-chamber syringe device, it being possible for the connection to be additionally sealed by a sealing ring (21). When the part-cylinder (2c) is attached, positive pressure is not produced in chamber A, since the trapped air can escape through the membrane (8).

The part-cylinder (2c) can be filled via an opening that is the size of the entire inner diameter of the part-cylinder (2c). This makes the filling of solid components in particular possible in a simplified manner, without filling through the distal outlet opening (5a) and subsequent lyophilizing being necessary.

You are referred to example 1 for the description of use.

DESIGNATIONS

A chamber between the closure element (6) and the plunger (3) and bounded by the wall of the cylinder element (2)

B chamber between the plunger (3) or (3a) and the plunger (4) and bounded by the wall of the cylinder element (2)
1 two-chamber syringe device
2 cylinder element
2a cylinder
2b first, distal part-cylinder
2c second, proximal part-cylinder
3 distal plunger
3a additional plunger as closure of the proximal part-cylinder (2c)
4 proximal plunger
5a distal outlet opening in the cylinder (2a)
5b proximal opening in the cylinder (2a)
5c proximal opening in the first, distal part-cylinder (2b)
5d distal opening in the second, proximal part-cylinder (2c)
6 closure element of the outlet opening (5a)
7 bore
7a shoulder
7b venting channel
8 fluid-tight, gas-permeable membrane
8a frame for fixing the membrane (8)
8b orifice plate
9 transfer channel (bypass)
10 spacer ring
11 sealing disk
12 fixing sleeve
12a bore in the fixing sleeve (12)
13 formed threaded part
14 protective cap
15 valve membrane
15a punched cut or punched opening in the valve membrane (15)
15b opened position of the valve membrane (15) when gas passes through
16 solid or liquid component in chamber A
17 liquid component in chamber B
18 axial groove
19 stop
20 screw connection
21 sealing ring
22 offset at the proximal end of the part-cylinder (2b)
23 widening at the distal end of the part-cylinder (2c)
24 connecting zone of the part-cylinders (2b)//(2c)

What is claimed is:

1. A two-chamber syringe device comprising
    a) a cylinder element (2) with a distal outlet opening (5a), a proximal opening (5b) and one or more transfer channels (9),
    b) a closure-element (6) of the distal outlet opening (5a) comprising a needle pierceable sealing disk (11) placed onto the outlet opening of the cylinder element and a fixing sleeve (12) enclosing the needle pierceable sealing disk (11), and
    c) a distal plunger (3) and a proximal plunger (4), which can be introduced into the cylinder element (2), a chamber being formed between the closure element (6) and the distal plunger (3) inside the cylinder element (2),
    wherein one or more fluid-tight, gas-permeable membranes (8) are arranged in the wall of the cylinder element (2).

2. The two-chamber syringe device as claimed in claim 1, wherein the cylinder element (2) is formed as one part and comprises a cylinder (2a).

3. The two-chamber syringe device as claimed in claim 1, wherein the cylinder element (2) is formed as two parts and comprises the distal part-cylinder (2b) and the proximal part-cylinder (2c).

4. The two-chamber syringe device as claimed in claim 3, wherein, between plungers (3) and (4), a further plunger (3a) is arranged at the distal end of the proximal part-cylinder (2c).

5. The two-chamber syringe device as claimed in claim 1, the closure element (6) including an element for fastening a needle.

6. The two-chamber syringe device as claimed in claim 1, the closure element (6) including a spacer ring (10), which is positioned between the sealing disk (11) and the cylinder element (2), and optionally includes a sealing ring (21) between the spacer ring (10) and the cylinder element (2).

7. The two-chamber syringe device as claimed in claim 1, the two-chamber syringe device including a protective cap (14) for fitting onto the distal end of the cylinder element (2) and/or the distal end of the closure element (6).

8. The two-chamber syringe device as claimed in claim 1, wherein a fluid-tight, gas-permeable membrane (8) is arranged in the wall of the cylinder element (2) at the distal end of the cylinder element (2) in the region of the chamber.

9. The two-chamber syringe device as claimed in claim 1, wherein the fluid-type, gas-permeable membrane (8) is arranged in the closure element (6).

10. The two-chamber syringe device as claimed in claim 9, wherein the sealing disk (11) represents the fluid-type, gas-permeable membrane (8).

11. The two-chamber syringe device as claimed in claim 1, wherein a valve element (15) is arranged over the fluid-tight, gas-permeable membrane (8).

12. The two-chamber syringe device as claimed in claim 1, wherein a fluid-tight, gas-permeable membrane (8) comprises a sterile filter membrane.

13. The two-chamber syringe device as claimed in claim 12, the sterile filter membrane having a pore size of less than or equal to 0.2 pm.

14. The two-chamber syringe device as claimed in claim 1, wherein the chamber contains a solid component and a proximal chamber B contains a liquid component.

15. The two-chamber syringe device as claimed in claim 1, wherein both the chamber and a chamber contain a liquid component.

16. The two-chamber syringe device as claimed in claim 1, wherein the syringe device comprises a carpule.

17. The two-chamber syringe device as claimed in claim 1, wherein the syringe device comprises a disposable syringe, a needle intended for piercing the sealing disk (11) being fastened to the distal end of the cylinder element (2), and the syringe device including a device for moving the plunger (4) in the distal direction.

18. An outer packaging for a two-chamber syringe device as claimed in claim 1, wherein the outer packaging is produced from a gas-tight sheet material.

19. The outer packaging as claimed in claim 18, wherein the outer packaging material comprises aluminum foil, plastic-laminated aluminum foil or aluminum-coated plastic film.

20. An applicator including a two-chamber syringe device as claimed in claim 1, a needle for attaching to the distal end of the cylinder element (2).

21. A two-chamber syringe device comprising
a) a cylinder element (2) with a distal outlet opening (5a), a proximal opening (5b) and one or more transfer channels (9),
b) a closure-element (6) of the distal outlet opening (5a) comprising a needle pierceable sealing disk (11) placed onto the outlet opening of the cylinder element and a fixing sleeve (12) enclosing the needle pierceable sealing disk (11), and
c) a distal plunger (3) and a proximal plunger (4), which can be introduced into the cylinder element (2), a chamber being formed between the closure element (6) and the distal plunger (3) inside the cylinder element (2), and
d) a fluid-tight, gas-permeable membrane (8) are arranged laterally in the closure element (6).

22. The two-chamber syringe device as claimed in claim 21, wherein the syringe device comprises a carpule.

23. The two-chamber syringe device as claimed in claim 21, wherein the closure element (6) comprises an element for fastening a needle for use with an injector system.

24. The two-chamber syringe device as claimed in claim 23, wherein the injector system comprises a pen system.

25. The two-chamber syringe device as claimed in claim 21,
wherein the syringe device comprises a disposable syringe, a needle intended for piercing the sealing disk (11) being fastened to the distal end of the cylinder element (2), and the syringe device further comprising a device for moving the plunger (4) in the distal direction.

26. A two-chamber syringe device comprising
a) a cylinder element (2) comprising a distal outlet opening (5a), a proximal opening (5b) and a transfer channel (9),
b) a closure-element (6) of the distal outlet opening (5a) comprising a needle pierceable sealing disk (11) placed onto the outlet opening of the cylinder element and a fixing sleeve (12) enclosing the needle pierceable sealing disk (11), and
c) a distal plunger (3) and a proximal plunger (4), which can be introduced into the cylinder element (2), a chamber being formed between the closure element (6) and the distal plunger (3) inside the cylinder element (2), and
d) a fluid-tight, gas-permeable membrane (8) arranged laterally in the closure element (6) in addition to the sealing disk (11).

27. The two-chamber syringe device as claimed in claim 26, wherein the syringe device comprises a carpule.

28. The two-chamber syringe device as claimed in claim 26, the closure element (6) comprising an element for fastening a needle.

29. The two-chamber syringe device as claimed in claim 26,
wherein the syringe device comprises a disposable syringe, a needle intended for piercing the sealing disk (11) being fastened to the distal end of the cylinder element (2), and the syringe device including a device for moving the plunger (4) in the distal direction.

* * * * *